(12) United States Patent
Cosentino et al.

(10) Patent No.: US 8,766,789 B2
(45) Date of Patent: Jul. 1, 2014

(54) FIRST EMERGENCY RESPONSE DEVICE

(75) Inventors: Daniel L. Cosentino, Excelsior, MN (US); Brian A. Golden, Eden Prairie, MN (US); Christopher T. Abrahamson, Bloomington, MN (US); Louis C. Cosentino, Excelsior, MN (US)

(73) Assignee: Cardiocom, LLC, Minneapolis, MN (US)

( * ) Notice: Subject to any disclaimer, the term of this patent is extended or adjusted under 35 U.S.C. 154(b) by 342 days.

(21) Appl. No.: 13/250,642

(22) Filed: Sep. 30, 2011

(65) Prior Publication Data
US 2013/0082837 A1    Apr. 4, 2013

(51) Int. Cl.
*G08B 1/08* (2006.01)
(52) U.S. Cl.
USPC .................................................. 340/539.12
(58) Field of Classification Search
USPC ........ 340/539.12, 573.1, 13.24; 600/300, 301
See application file for complete search history.

(56) References Cited

U.S. PATENT DOCUMENTS

| | | | |
|---|---|---|---|
| 4,835,372 A | 5/1989 | Gombrich et al. | |
| 4,916,441 A | 4/1990 | Gombrich | |
| 5,019,974 A | 5/1991 | Beckers | |
| 5,339,821 A | 8/1994 | Fujimoto | |
| 5,465,082 A | 11/1995 | Chaco | |
| 7,733,224 B2* | 6/2010 | Tran | 340/540 |
| 2003/0050054 A1 | 3/2003 | Siu | |
| 2005/0075116 A1 | 4/2005 | Laird et al. | |
| 2005/0231375 A1* | 10/2005 | Kingston | 340/574 |
| 2006/0106290 A1* | 5/2006 | Bulat | 600/300 |
| 2008/0117060 A1* | 5/2008 | Cuddihy et al. | 340/573.1 |
| 2010/0295684 A1* | 11/2010 | Hsieh et al. | 340/573.1 |

OTHER PUBLICATIONS

Hughes, "Bedside Terminals: Clinicom," *Clinical Computing*, vol. 5, No. 1 pp. 3 and 22-28 (1988).
International Search Report and Written Opinion for PCT/US2012/057896 mailed Feb. 13, 2013.

* cited by examiner

*Primary Examiner* — Phung Nguyen
(74) *Attorney, Agent, or Firm* — Girma Wolde-Michael; Evans M. Mburu

(57) ABSTRACT

A personal emergency device is provided to individuals to allow the individuals to request emergency assistances. The device communicates with a base receiver to indicate the individual has requested assistances. The base receiver then communicates with an emergency system such as e-911 emergency services or a remote care system. The base receiver or the remote care system may forward information to the emergency services to provide first responders with additional information regarding the individual. The information may include personal information such as age and name, and the information may include medical information such as a recent blood pressure, weight, and blood glucose level.

10 Claims, 35 Drawing Sheets

FIRST EMERGENCY RESPONSE DEVICE

CROSS REFERENCE TO RELATED APPLICATIONS

The following commonly-assigned patent applications have at least some subject matter in common with the current application:
Ser. No. 29/403,118 entitled "Wireless Remote", filed Sep. 30, 2011.

TECHNICAL FIELD

The instant disclosure relates to emergency devices. More specifically, the instant disclosure relates to a device for invoking an emergency response.

BACKGROUND

When an individual encounters an emergency, the individual dials an emergency service such as 911, and the emergency service arranges for assistance to be provided to the individual. However, conditions may arise under which the individual is unable to reach a phone to dial 911. For example, when an individual suffers from a medical condition such as a heart attack, the individual may be unable to reach a telephone. In another example, when an individual falls and breaks a bone, the individual may be unable to reach a telephone. These situations are more likely to occur when individuals are alone, because no one else is available to assist the individual.

Additionally, even when the individual is able to reach a telephone to dial 911 emergency services, the individual may be unable to communicate with the 911 operator. For example, if the individual suffers a heart attack, as described above, the individual may be unable to speak. The 911 operator may have access to a limited amount of information from which to assess the individual and decide on an appropriate response by the emergency services.

SUMMARY

According to one embodiment, a method includes receiving an emergency notification from a personal emergency device. The method also includes contacting an emergency system after receiving the emergency notification. The method further includes transmitting medical information about a user associated with the remote device to the emergency system.

In further embodiments, contacting the emergency system includes contacting a remote care system. In another embodiment, transmitting information may include transmitting personal information and/or medical information regarding the user, in which the medical information may be obtained from a personal medical device. In yet another embodiment, contacting the emergency system may include contacting an emergency service. In a further embodiment, the emergency notification may be transmitted with a wireless signal such as a Bluetooth device.

According to another embodiment, a method includes receiving an emergency notification from a remote device. The method also includes evaluating medical information corresponding to a user of the remote device. The method further includes determining whether the user requires the assistance of an emergency service. The method also includes contacting an emergency service when the user is determined to require assistance. The method further includes transmitting medical information regarding the user to the emergency service.

In further embodiments, the method may also include receiving medical information corresponding to the user from personal medical devices before the step of evaluating the medical information, in which the medical information includes at least one of personal information, medical history, blood pressure, weight, and blood glucose levels. The medical information may be stored in a database server. In another embodiment, the step of determining whether the user requires assistance may include providing the medical information to a nurse and receiving feedback from the nurse regarding the user. In yet another embodiment, the method may include notifying a primary caregiver for the user of the emergency notification after contacting emergency services.

According to yet another embodiment, a system includes a personal emergency device having a wireless transmitter and an emergency notification button. The system also includes a base receiver having a wireless receiver coupled to the wireless transmitter and a first communications link to an emergency system. The base receiver also includes a processor configured to receive an indication from the remote that the emergency notification button was activated. The processor is also configured to contact an emergency system after receiving the indication. The processor is further configured to transmit medical information about a user associated with the remote to the emergency system.

In further embodiments, the base receiver may also include a second communications link to a personal medical device, in which the processor is further configured to receive medical information from the personal medical device and to transmit the medical information to the emergency system. In another embodiment, the wireless transmitter comprises a Bluetooth transmitter and the wireless receiver comprises a Bluetooth receiver. IN yet another embodiment, the emergency system may be an emergency service or a remote care system. A remote care system may include a database server and a processor coupled to the database server, in which the processor is configured to receive the medical information from the base receiver, to store the medical information in the database server, and to determine from cumulative medical information in the database server whether the user requires the attention of an emergency service.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying configured. It is to be expressly understood, however, that each of the configured is provided for the purpose of illustration and description only and is not intended as a definition of the limits of the present invention.

BRIEF DESCRIPTION OF THE DRAWINGS

For a more complete understanding of the disclosed system and methods, reference is now made to the following descriptions taken in conjunction with the accompanying drawings.

DETAILED DESCRIPTION

In general, emergency assistance may be requested by a user through a personal emergency device. When the user requires emergency assistance, such as when the user suffers a heart attack or falls down and is unable to get up, the user presses the button on the personal emergency device. The personal emergency device transmits a signal to a base station. The base station sends a signal to request assistance for the user from an emergency system. Medical information and/or personal information may be transmitted to the emergency system along with the request for assistance to provide first responders with pertinent information before reaching the user. The additional information can ensure the first responders are adequately prepared to handle the emergency allow the first responders to provide higher quality assistance to the user, or to provide other assistance, such as have the hospital ready for the particular patient.

Systems for Providing Emergency Response

Figure 1:
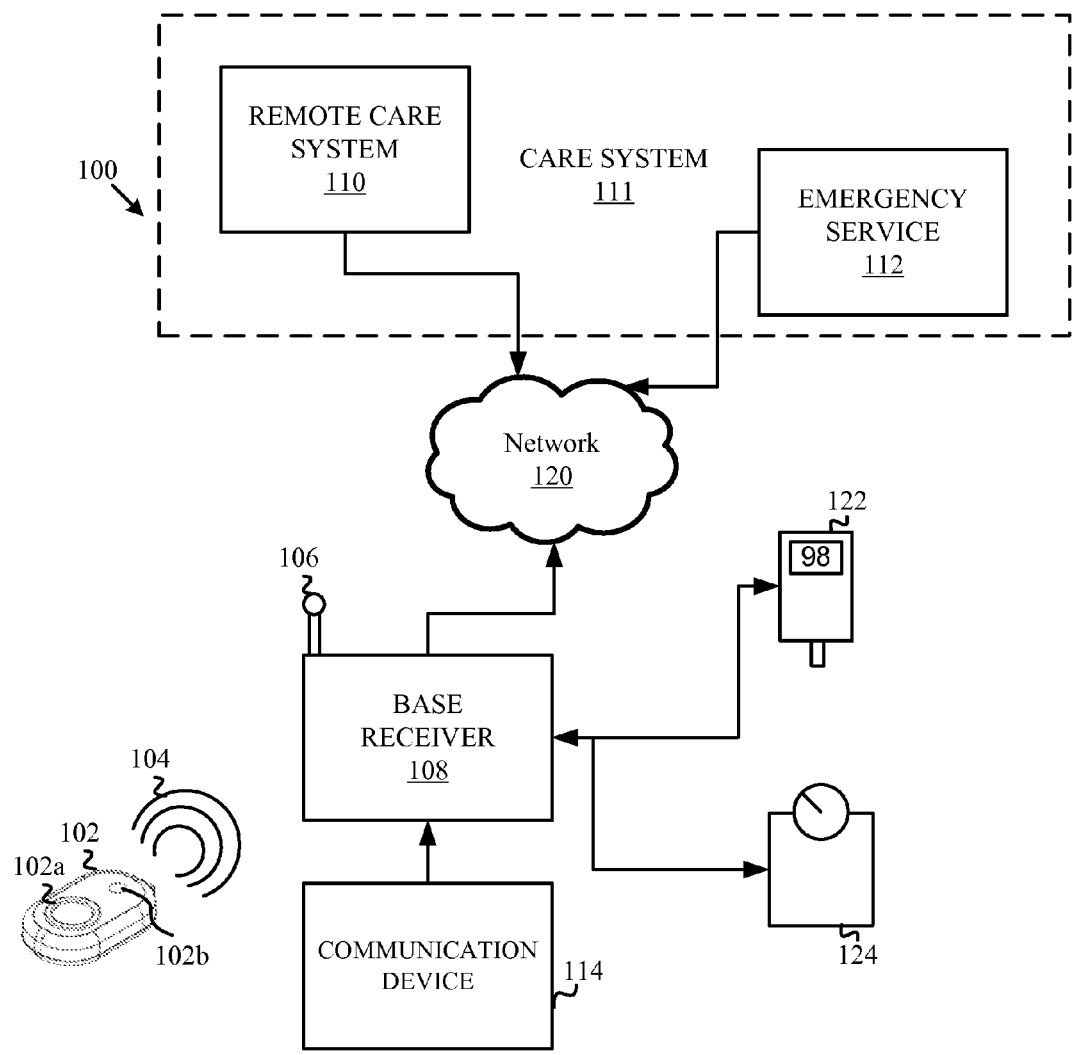
FIG. 1 is a block diagram illustrating a system including a personal emergency device according to one embodiment.

FIG. 1 is a block diagram illustrating a system 100 including a personal emergency device according to one example embodiment. The system 100 includes a personal emergency device 102 accessible by a user or held in close proximity to the user. Preferably, the device 102 includes a button 102*a* for activation by a user to request emergency assistance. The device 102 may also include an indicator 102*b* for providing feedback to the user. For example, the indicator 102*b* may glow green when the device 102 is powered and connected, i.e. wirelessly, to a base receiver 108. The indicator 102*b* may blink green after the button 102*a* is activated to indicate to the user that the request for emergency assistance has been received. The indicator 102*b* may also blink faster to indicate to the user that the request for emergency assistance has been received and help is on the way. The indicator 102 may turn red to indicate that a problem has occurred with the device 102. The indicator 102 may blink red to indicate that the device 102 has a low battery.

The device 102 includes a wireless transmitter for transmitting wireless signals 104 to a base receiver 108. The wireless transmitter may be, for example, one or more of a Bluetooth transmitter, a ZigBee transmitter, an IEEE 802.11 WiFi transmitter, a radio frequency (RF) transmitter, an infrared (IR) transmitter, or other suitable transmitter. In one example embodiment, the device 102 can include a microprocessor for receiving input from the user through the button 102a, providing feedback to the user through the indicator 102b, and operating the wireless transmitter to transmit the wireless signals 104. The device 102 can also include a receiver for receiving feedback from the base receiver 108. The device 102 can also include a lock switch (not shown) for preventing accidental activation of the button 102a.

In certain embodiments, the device 102 can have an unobstructed transmission range of up to or exceeding 250 feet, can be water-resistant to allow use in a shower, bathtub, or garden, can have a battery life of one or more years, can be constructed from plastic and/or rubber materials, can weigh less than one ounce, and can be shock-resistance and durable.

In further embodiments, the device 102 can include additional features. For example, the device 102 may include a microphone, speaker, or video camera to allow communication between the user of the device 102 and an emergency system. In another example, the device 102 may include an accelerometer to automatically detect falls or other conditions experienced by a user. In yet another example, the device 102 may include an ambient temperature sensor, skin temperature sensor, or pulse sensor.

The device 102 may be worn by the user attached to a necklace, a belt clip, or carried in a pocket. According to one embodiment, the device 102 may be integrated with another wireless device. For example, the device 102 may be integrated into a Bluetooth device coupled to a mobile phone, such that an emergency service 112 can call the mobile phone and communicate directly with the user. In another example, the device 102 may be integrated into a blood glucose meter carried by the user. In yet another example, the device 102 may be integrated into a watch, or wrist device, worn around the wrist, in which the watch includes a pulse sensor or temperature sensor that provides information to the device 102 for relay to a base receiver 108.

Figure 2:
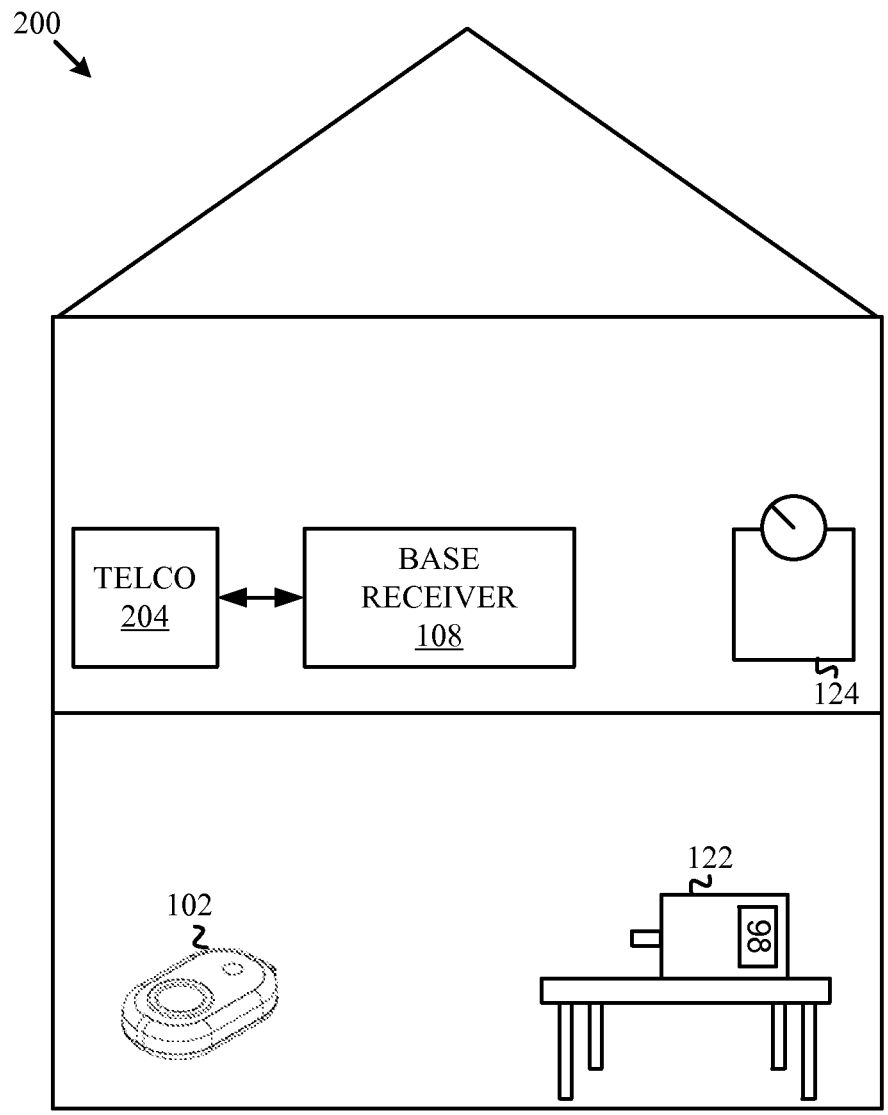
FIG. 2 is a block diagram illustrating an installation of a base receiver in a house according to one embodiment.

Preferably, wireless signals 104 are transmitted by a wireless transmitter of the device 102 and received by a wireless receiver 106 of the base receiver 108. The base station 108, described in more detail below in other example embodiments, may function as a command center, or hub, for one or more devices located in a common area. For example, as shown in FIG. 2, the base receiver 108 may be located inside a house 200 along with the personal emergency device 102 and other personal medical devices 122, 124. FIG. 2 is a block diagram illustrating an installation of a base receiver in a house according to one embodiment. Other devices coupled to the base receiver 108 may include a weight scale 124, a blood glucose meter 122, a blood pressure monitor (not shown), a pulse monitor (not shown), and/or exercise equipment (not shown) such as a treadmill. Additional details regarding these devices are disclosed in U.S. application Ser. No. 12/330,837, entitled "Glucose Meter System and Monitor", and U.S. application Ser. No. 10/746,325, entitled "Weight loss or weight management system," which are hereby incorporated by reference.

Preferably, the base receiver 108 function as a gateway between the devices 102, 122, and 124 and a care system 111. The care system 111 can comprise an emergency system such as an emergency service 112 and/or a remote care system 110. And, the emergency service 112 can be a part of the remote care system 110. Preferably, the remote care system 110 is a remote monitoring service for monitoring patients having a chronic disease. The emergency device 102 could be a button on the base receiver 108. Communications between the devices 122 and 124 and the base receiver 108 may be wireless, as communication with the device 102, or may be through wired connections in the house 200 such as power lines, phone lines, and/or network lines.

The base receiver 108 can be coupled to a telco device 204 for connecting to an emergency system such as the emergency service 112 and/or the remote care system 110. For example, the telco device 204 may be an access point for a public switched telephone network (PSTN), an internet connection such as a cable modem or a digital subscriber line (DSL) modem, or a wireless internet connection such as a WiFi device or a cellular network device such as a 3G or 4G hotspot. In one embodiment, the telco device 204 may be integrated with the base receiver 108 in a single package such that the base receiver 108 can be directly connected via a telephone line, wireless connection, or Ethernet port to a network 120, such as the Internet.

The base receiver 108 can include connections to other devices or include the devices themselves integral with the base receiver 108. For example, the base receiver 108 can include video and audio inputs for connecting to a camera, a microphone, or a motion detector. The video and audio inputs can include conventional composite connections or network ports for connecting with IP-based cameras and microphones. The base receiver 108 can also include an output for a video device and an input for an input device. The base receiver 108 can interact with a user through the video device and the input device for interacting with the user to perform tasks such as reviewing and/or analyzing data collected from the devices 102, 122, and 124 and/or configuring the devices 102, 122, and 124. Additionally, the base receiver 108 can provide a web-based interface allowing the user to access data and be configured to devices 102, 122, and 124 through their computer or cellular phone by typing an appropriate web address into a web browser or custom software installed on the computer or cellular phone.

Although the base receiver 108 is shown in FIG. 2 as a gateway for the devices 102, 122, and 124 in the house 200, use of the base receiver 108 is not limited to single residences. For example, the base receiver 108 may be installed in a multi-family dwelling such as an apartment complex, a retirement community, a hospital, or any place within suitable range.

Referring back to FIG. 1, the base receiver 108 communicates through a network 120 with the remote care system 110 and/or the emergency service 112. Alternatively, the base receiver 108 could communicate with other entities, i.e. a family member. The emergency service 112 can be part of the remote care system 110 or a separate call center for handling emergency calls. Typically, the base receiver would not directly communicate with a 911 service. Preferably, when a user pushes the button 102a, the emergency device 102 transmits a wireless signal 104 to the wireless receiver 106 of the base station 108. The base station 108 recognizes the signal as an emergency signal and places a call, or transmits a signal, to the remote care system 110 and/or the emergency service 112 for immediate help. In one example embodiment, the base receiver 108 would transmit a signal to the remote care system 110.

The remote care system 110 can attempt to determine if the signal is a false alarm or not. For example, the remote care system 110 could place a call to the user or access a camera in the user's house. If the signal is a false alarm, the remote care system 110 would take no further action. If the signal is not false, the remote care system 110 would initiate the call to the emergency service 112 and can also provide additional information to the emergency service 112, such as the patient's medical history, trended data collected through the base receiver 108 (discussed in more detail below), exception reports (discussed in more detail below), or current data available to the base receiver 108. The base receiver 108 can also communicate current medical information, such as blood pressure, weight, and requests for assistance, and personal information, such as name, age, and location to the remote care system 110. The medical information and personal information may be stored in database servers, described below with reference to FIG. 5, at the remote care system 110.

In another example embodiment, the base receiver 108 can send a signal to both the remote care system 110 and the emergency service 112. In another example embodiment, the base receiver 108 can send a signal to the emergency service 112, which may then contact the remote care system 110 to get information. Alternatively, the remote care system 110 can transfer information on a periodic basis to the emergency service 112. When a request for assistance is made through the personal emergency device 102 by activating the button 102a, the base receiver 108 contacts an emergency system such as the remote care system 110 and/or the emergency services 112.

Methods for Providing Emergency Response

Figure 3:
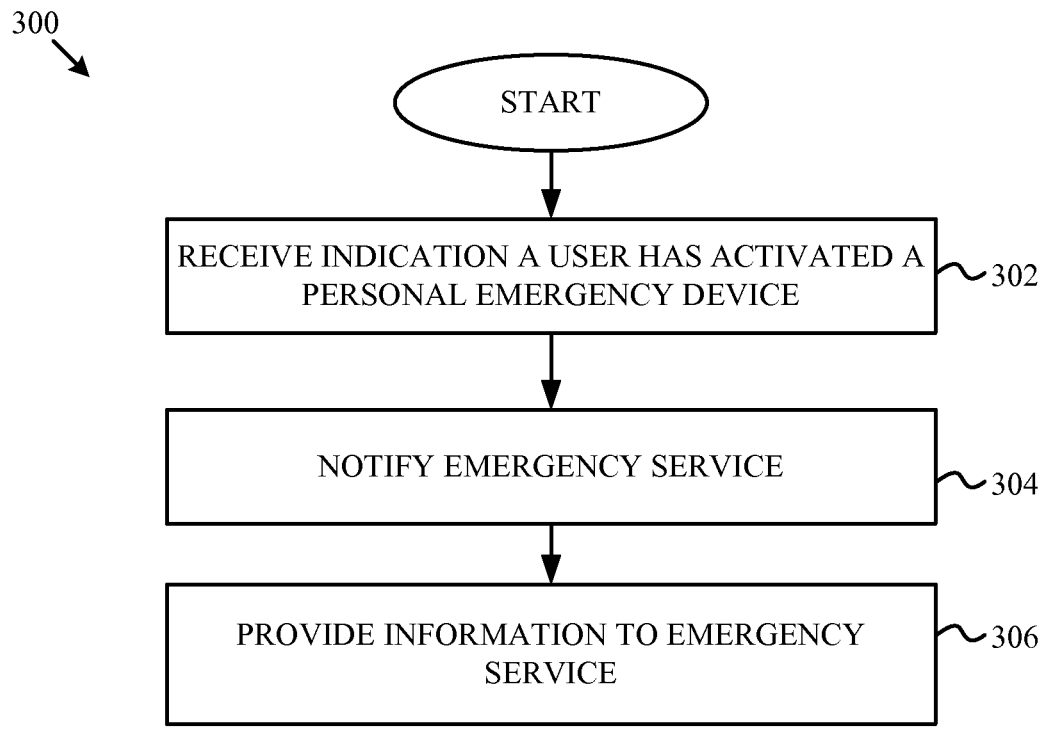
FIG. 3 is a flow chart illustrating a method for notifying emergency services according to one embodiment.

According to a preferred embodiment, the base receiver 108 notifies the emergency services 112 when the button 102a is activated. FIG. 3 is a flow chart illustrating a method for notifying emergency services according to one embodiment. A method 300 begins at block 302 with the base receiver, such as the base receiver 108 of FIG. 1, receiving an indication that a user has activated a personal emergency device, such as the personal emergency device 102 of FIG. 1. The method 300 continues to block 304 to notify an emergency service, which may be a call center for monitoring such calls. The method then proceeds to block 306 to provide information to the emergency service. The information provided to the emergency service at block 306 may include medical information, personal information, and/or simply an identifier of some type. For example, the emergency service may be provided with medical information such as the user's most recent weight, blood pressure, and blood glucose level available to the base receiver 108, or trended medical data collected over time by the base receiver 108 and stored by the remote care system 110 (thus there would be communication between the remote care system 110 and the emergency service 112 at least on a periodic basis) The emergency service 112 may also be provided with personal information such as the user's age and contact information for relatives and primary medical caregivers.

In a preferred embodiment, the base receiver 108 would make a call to the emergency service 112 and transmit a device identifier. The emergency service 112 can then pull up pertinent records associated with that device identifier. Such records could include name, address, past medical history, trended medical history, current medical information, emergency contact instructions or information, etc. . . .

Any devices currently monitoring the user or the user's environment (i.e. a temperature sensor, motion sensors, cameras, smoke alarms, etc.) may be polled by the base receiver 108 to acquire new information if available and the new information may be passed to the emergency service 112. Historical medical information stored in the base receiver 108 or at the remote care system 110 may also be transmitted to the emergency service 112. For example, the base receiver could also cause a signal to go to the remote care system 110 notifying it that emergency services 112 has been contacted and that certain information needs to be transmitted to emergency services 112. Alternatively, emergency services 112 could make a call to the remote care system 110 to collect such information.

The remote care system 110 can record the emergency event as part of the patient's stored medical history. Such event may prompt further follow-up from a nurse or other caregiver. In addition, the base receiver 108 could be connected to a communication device 114, such as a speaker phone, a video phone, or other communication device that is either separate from the base receiver 108 or integral with the base receiver 108. When the base receiver 108 sends the signal out to the emergency service 112, the base receiver 108 could activate the speaker phone 114 to answer the next phone call. When the emergency service 112 calls the house of the user to verify the emergency, the speaker phone 114 is activated to automatically pick up the call such that the emergency services 112 may be able to directly communicate with the user. Alternatively, the communication device 114 could place the call to the emergency service 112. In addition, the emergency service 112 can patch in an appropriate nurse or doctor or staff at the remote care system 110 to help assess the patient's needs.

Figure 4:
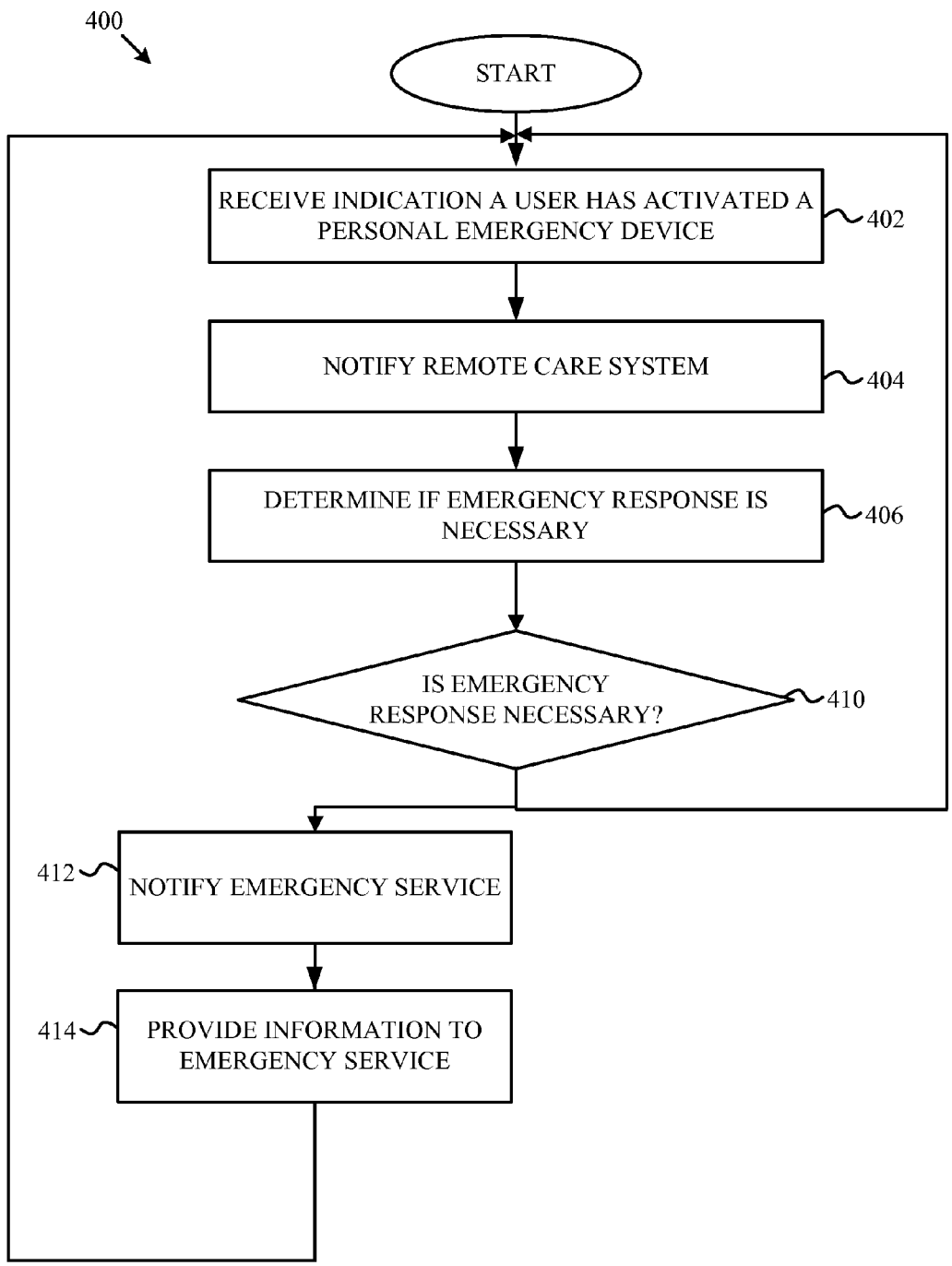
FIG. 4 is a flow chart illustrating a method for notifying emergency services according to another embodiment.

According to another embodiment, the base receiver 108 notifies the remote care system 110 when the button 102a is activated. FIG. 4 is a flow chart illustrating a method for notifying emergency services according to another embodiment. A method 400 begins at block 402 with receiving an indication that a user has activated a personal emergency device. The method 400 continues to block 404 with notifying the remote care system. The notification to the remote care system may include a specific identifier assigned to the personal emergency device, which allows the remote care system to determine the user assigned to the personal emergency device. For example, a database server in the remote care system may have records linking personal emergency devices assigned to specific individuals. While notifying the remote care system of activation of the personal emergency device, the base receiver may also transmit medical information for the user. For example, the base receiver may transmit a recent weight, blood pressure, and/or blood glucose level. The base receiver may also poll a device after receiving the indication that the personal emergency device was activated to obtain new information that may be available for transmission to the remote care system.

The method 400 continues to block 406 where the remote care system determines if an emergency response is necessary. The remote care system may use an algorithm to examine the medical information and personal information available in the database servers to determine if an emergency response is necessary. The algorithm may consider current values for medical information, historical values for medical information, and trends in the medical information. Preferably, the remote care system includes staff, i.e. doctors, nurses, or other trained professions, to evaluate the user when the remote care system is notified of an activated personal emergency device. The staff may attempt to contact the user through messages or telephone calls to obtain additional information or to determine if a false alert occurred. In addition, an interactive voice response (IVR) system could be used to contact the user. The remote care system can activate cameras, motion detectors, or microphones in the user's home to try to assess the situation.

The staff may receive access to video cameras and/or microphones connected to the base receiver to check on the status of the user. The video cameras and microphones may otherwise be unavailable to staff at the remote care system. However, when the personal emergency device is activated the video cameras and microphones are temporarily made available to the staff. In another embodiment, the base receiver may activate the video camera and microphone and record input for a short duration and transmit the recorded video and audio for transmission to the remote care system.

The method 400 continues to block 410 to determine if an emergency response is necessary. If an emergency response is determined to be necessary, then the method 400 continues to block 410 to notify emergency services or 911. According to one embodiment, the remote care system contacts the emergency service on behalf of the user. According to another embodiment, the remote care system authorizes the base receiver to contact the emergency service for the user. When the base receiver is configured to contact the emergency service for the user, the base receiver may include a time-out option, such that if no response is received from the remote care system within a period of time after the personal emergency device is activated, then the base receiver automatically contacts the emergency services for the user.

After notifying emergency services at block 412, information is provided to the emergency service at block 414. The information provided at block 414 may include medical information and personal information. The information may be provided by the base receiver and/or the remote care system. The information may be relayed by the emergency service to first responders, such that the first responders are adequately prepared to handle the emergency experienced by the user. For example, the first responders may receive data suggesting the user has suffered a heart attack. Thus, the first responders will know to have a defibrillator available.

According to one embodiment, the remote care system may also provide information to a primary caregiver for the user. For example, the remote care system may search the database servers to identify doctors who have treated the user. The remote care system may identify one of the doctors as a primary caregiver and notify the primary caregiver that the user has requested emergency assistance. The remote care system may also connect the primary caregiver to the first responder or provide the primary caregiver of the location to which the user is being transported so that the primary caregiver may arrive at the location with the user. Additionally, the hospital or care facility can be notified that the patient is on her way.

Emergency Response for Congestive Heart Failure

The emergency response device described above may be provided to patients suffering from chronic diseases, such as congestive heart failure, that are being routinely monitored by a remote monitoring system, such as the remote care system 110 of FIG. 1. These patients normally undergo drug therapy and lifestyle changes to manage their medical condition. In these patients, the medical professional caregiver monitors certain wellness parameters and symptoms including: weakness, fatigue, weight gain, edema, dyspnea (difficulty breathing or shortness of breath), nocturnal cough, orthopnea (inability to lie flat in bed because of shortness of breath), and paroxysmal nocturnal dyspnea (awakening short of breath relieved by sitting or standing); and body weight to measure the response of drug therapy. Preferably, the wellness parameters and symptoms are remotely monitored through equipment such as the personal medical devices 122, 124 of FIG. 1 and collected and transmitted by the base receiver 108 of FIG. 1. The information collected by these devices allows a medical professional caregiver to determine the effectiveness of the drug therapy, the patient's condition, whether the patient's condition is improving or whether the patient requires hospitalization or an office consultation to prevent the condition from getting worse. All of this information, including the doctors notes, are stored by, monitored and analyzed by the remote care system 110 and associated with the user. As such, the user can also be given an emergency device 102 to connect to its base receiver 108. When the user pushes the button 102, any or all of the collected data and/or the medical professional caregiver's opinions may be provided to first responders, the emergency service 112, a doctor, or a hospital in response to an emergency signaled by a personal emergency device 102 of FIG. 1.

Figure 5:
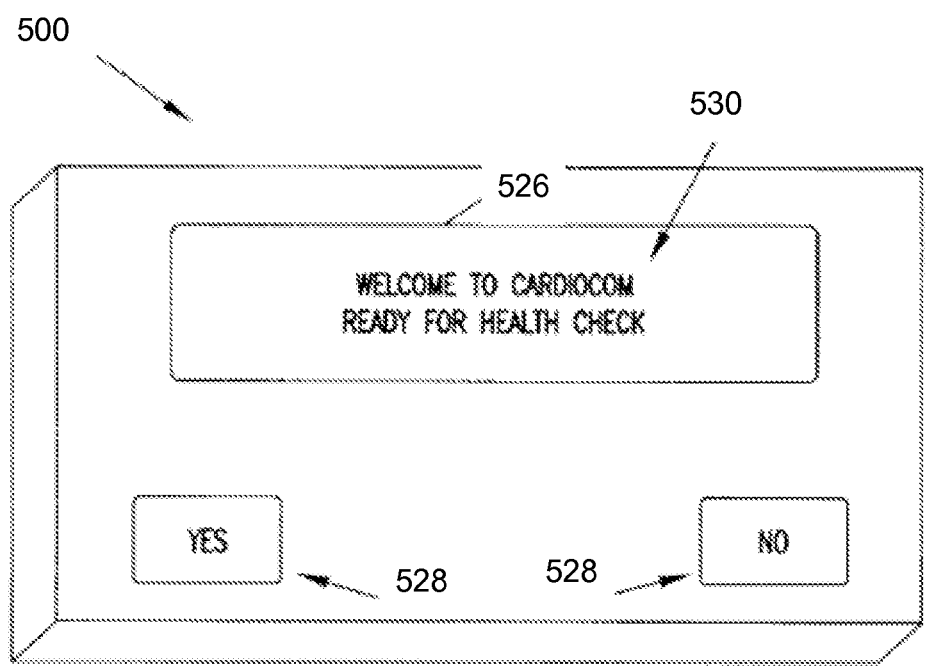
FIG. 5 is a block diagram illustrating a home monitoring apparatus according to one embodiment.

Information regarding a patient's health condition may be obtained prior to, during, or after the emergency response through a home monitoring apparatus 500 connected to or integrated with the base receiver 108 of FIG. 1. FIG. 5 is a block diagram illustrating a home monitoring apparatus according to one example embodiment. A patient home monitoring apparatus (e.g., the COMMANDER™ or TELESCALE™) outputs a message 530 such as "Welcome to Cardiocom. Ready for Health Check?" on the output display device 526. A patient will then proceed by selecting "Yes" or "No" on the touch pad 528. If the patient selects "Yes," the Health Check will begin. If the patient has selected "Yes," the patient will then answer a series of twelve Health Check questions (listed below) by pressing "Yes" or "No" on the keypad 528. An example list of questions that the patient may be queried on for a patient with chronic heart disease are as follows: 1) Are you feeling short of breath? 2) Are you coughing more than usual? 3) Are your ankles or feet swollen? 4) Does your stomach feel bloated? 5) Having more chest discomfort (angina)? 6) Are you urinating less than usual? 7) Are you more tired than usual? 8) Do you feel dizzy or lightheaded? 9) Are you taking your medication? 10) Are you reducing your sodium? 11) Did you exercise yesterday?

During the Health Check procedure, the patient will also be asked to weigh him/herself. Accordingly, the patient will be asked to step off the scale 124 of FIG. 1 so it can "auto-zero." At which time the message "000.0 lbs." will appear on the output display 526. Then, the patient will be asked to step on the scale 124 of FIG. 1. Next, the patient home monitoring apparatus 502 will display the patient's: 1) Current Weight (e.g., 155.0 lbs.); 2) Variance to Prior Day's Weight (e.g., gained 1.0 lbs.); 3) Maximum Allowed Weight (e.g., 150.0 lbs.); 4) Variance of Maximum Allowed Weight (e.g., exceeded Maximum Allowed Weight by 5.0 lbs.)

The Health Check is now complete and a message "Do you need to revise your answers?" will appear. This gives the patient an opportunity to revise any incorrect answers before transmission to a central computer system, such as the remote care system 110 of FIG. 1. If "No" is selected (e.g., no revisions), the data will be transmitted to the central computer system and the message "Thank you. Have a good day!" then "Your data is being transmitted" will appear on the display 126. If revisions are required and "Yes" is selected, the Health Check will be repeated.

The medical and personal information described in the Health Check procedure above may be stored on the remote care system 110 of FIG. 1 and transmitted to an emergency center 112 automatically at the activation of the button 102a or after review by a medical healthcare professional. All or some (e.g., the most recent) of the medical and personal information may be stored by the base receiver 108, which may transmit the data to the emergency service 112.

Remote Care System Operation

Figure 6:
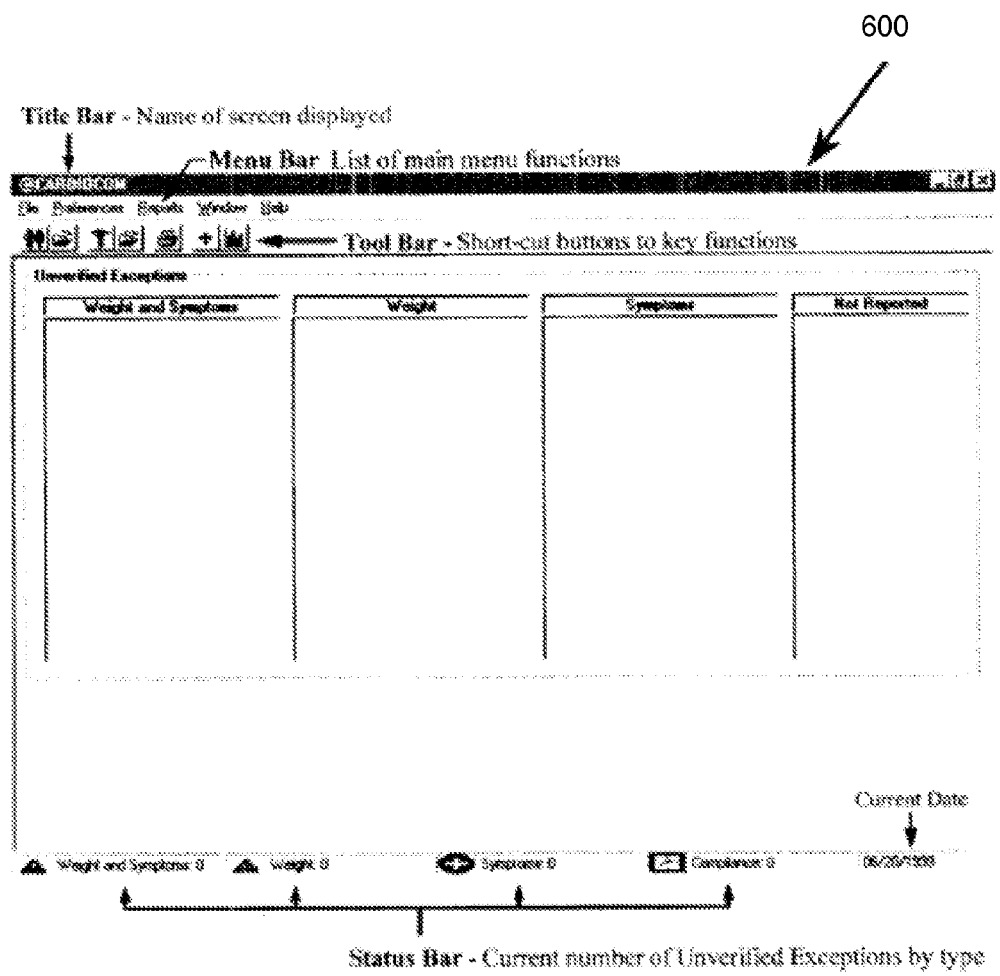
FIG. 6 is a screen shot illustrating a software program for monitoring and storing medical and personal information according to one embodiment.

FIG. 6 is a screen shot illustrating a software program for monitoring and storing medical and personal information at the remote care system 110, according to one example embodiment. A software screen 600 may include a toolbar including buttons that provide immediate access to frequently used commands and options may be provided to assist a system operator (or user) perform the patient monitoring, database management, etc. For example, the following functions may be executed by the user by clicking the appropriate icons embedded in the toolbar: 1) Open a New Patient Record 2) Edit an Existing Patient Record 3) Open a New Physician Record 4) Edit an Existing Physician Record 5) Print 6) View Exception Reports 7) View Trend Reports. The software program may operate on the base receiver 108 or the remote care system 110 of FIG. 1.

Figure 7A:
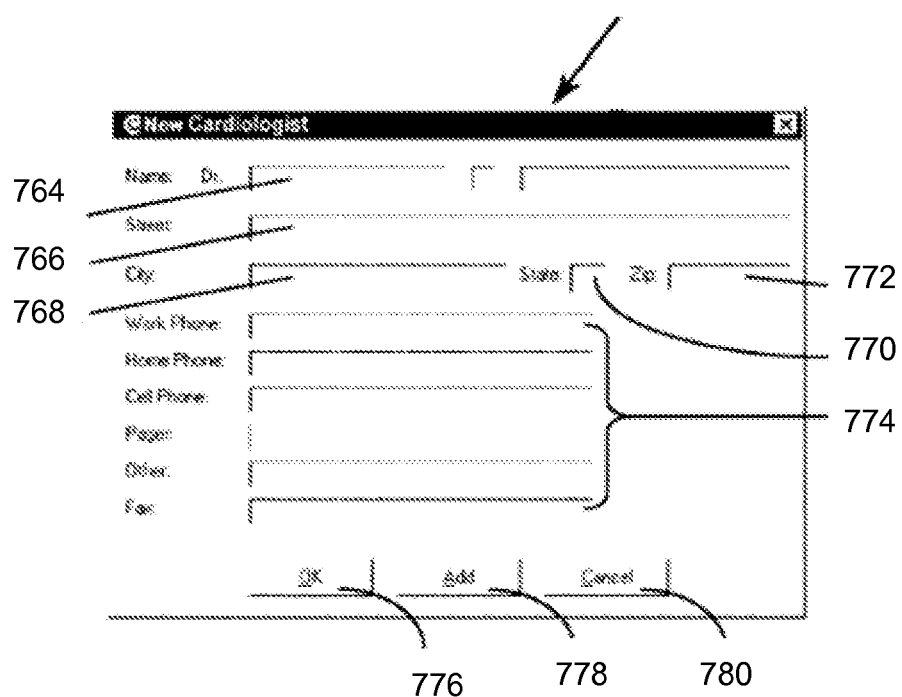
FIGS. 7A and 7B are screen shots illustrating a user screen according to one embodiment.
Figure 7B:
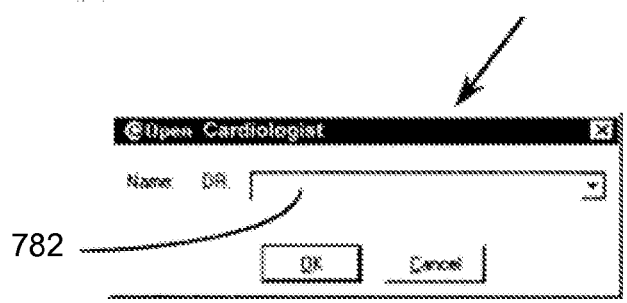

FIGS. 7A and 7B are screen shots illustrating a user screen according to one embodiment. The user screens may allow for performing the patient and medical professional caregiver record entry and edit function. A new "Physician Record" 762 is entered for each physician or health professional who will monitor patients and receive exception reports. The physician information in then entered in the appropriate fields. The following is an example of the information that may be entered in the Physician Record 762: 1) Name 764—First, Middle Initial, and Last Name 2) Street 766—Address including Street, Apartment, Suite, etc.; 3) City 768, State 770, Zip 772—City, State (2 letter abbreviation), and Zip; and 4) Phone 774—Work, Home, Cellular, Pager, Other and Fax numbers.

The user may then either return to the main menu or enter another physician record. The user presses OK 776 to enter the physician's record into the database 708 and return to the main menu. Alternatively, the user may then presses Add 778 to enter the physician's record into the database 708 and continue entering additional physician records. At any time the user may press Cancel 780 to stop and return to the main menu. Accordingly, no information will be entered.

To edit a Physician Record a user may select File, Open, Physician on the menu or may click on the appropriate icon. The user may then enter the physician's last name in the name box 782 or use the scroll-down menu 784 to locate a physician already contained in the database. Once the desired record is located, the user may select OK and the Edit Physician screen will be displayed. Accordingly, the user may then make any necessary changes in the physician record. Pressing OK will save the changes to the physician record. Pressing Cancel returns the user to the main menu.

Figure 8:
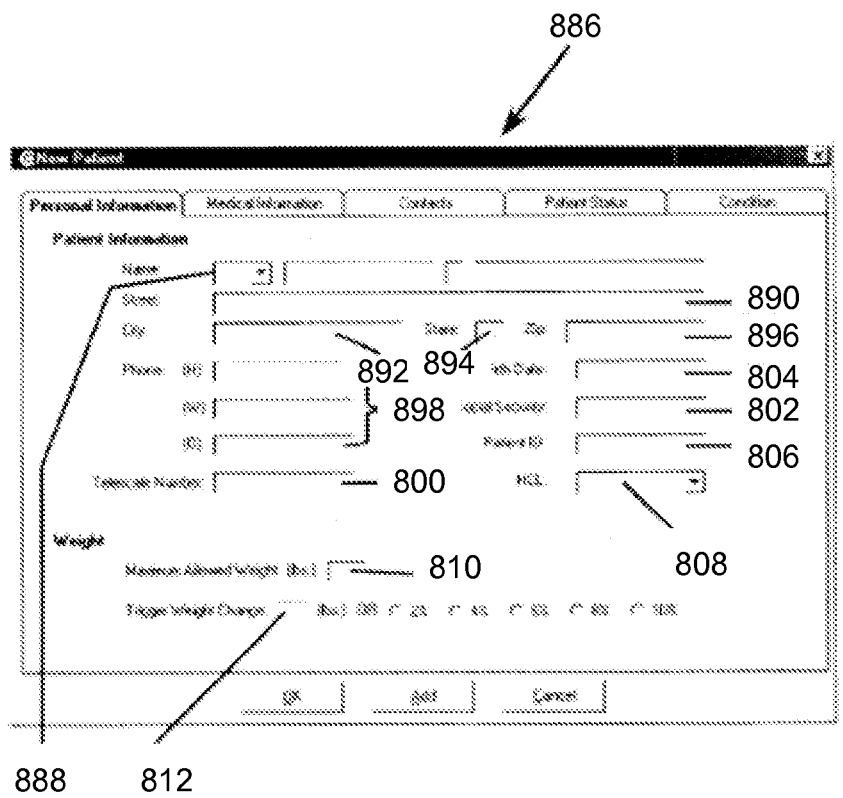
FIG. 8 is a screen shot a New Patient Record screen according to one embodiment.

FIG. 8 is a screen shot a New Patient Record screen 886 according to one embodiment. To Enter a New Patient Record the user may select File, New, Patient on the menu bar or may click on the appropriate icon. The patient's Personal Information in then entered in the appropriate fields. The following is an example of the information that may be entered in the New Patient Record: 1) Name 888—Title, (Mr., Mrs., Ms., Dr.), First, Middle Initial, and Last Name; 2) Street 890—Address including Street, Apartment, Suite, etc.; 3) City 892, State 894, Zip 896—City, State (2 letter abbreviation), and Zip; 4) Phone 898—Home, Work and Other Numbers; 5) TELESCALE Number 800—serial number assigned to the device; 6) Social Security 802—9 digit Social Security number; 7) Birth Date 804—Month/Day/Year (e.g., Jan. 29, 1940); 8) Patient ID 806—The user may designate any number or text field; and 9) HCL 808—This may be any number or text field for which the user needs a pull-down menu. In some facilities this number may be used to identify the patient's clinic.

The user may then proceed to enter additional patient Personal Information including the weight information specified by the physician (e.g., a Cardiologist). This information is also entered in the appropriate fields. The following is an example of the additional information that may be entered in the patient's Personal Information Record: 1) Maximum Allowed Weight 810 (lbs.)—This is the weight (lbs.) that the patient is instructed not to exceed; and 2) Trigger Weight Change 812 (lbs.) OR (%)—This is the variance in weight from the Maximum Allowed Weight that will prompt an Exception. If the patient's weight is greater than or equal to the Maximum Allowed Weight plus the Trigger Weight Change, an Exception Report should be printed and sent to the physician. The trigger Weight Change 812 may be entered in pounds (lbs.) or percent (%) of Maximum Allowed Weight.

Figure 9:
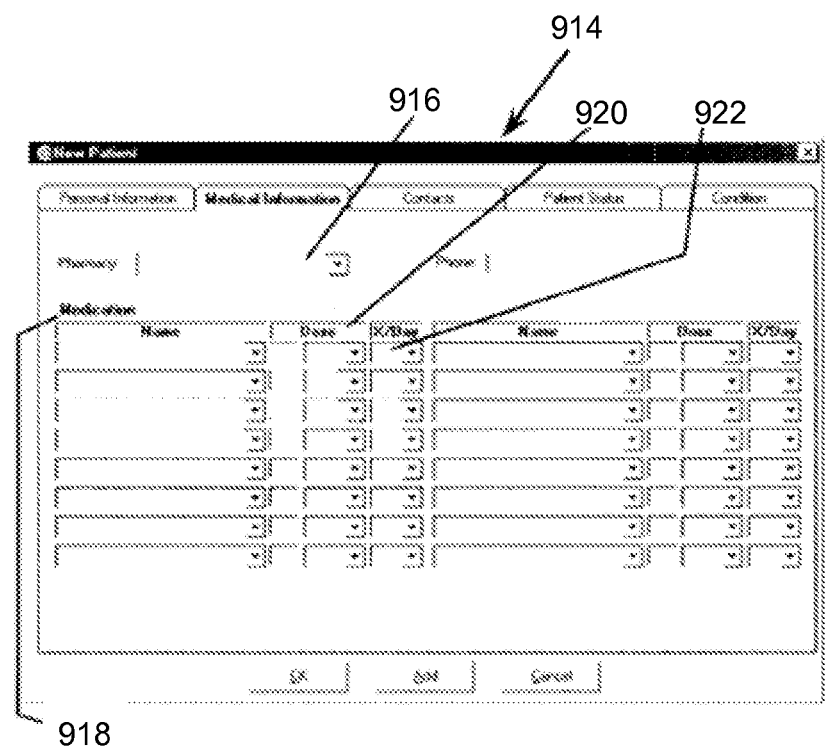
FIG. 9 is a screen shot illustrating a patient's Medical Information screen according to one embodiment.

FIG. 9 is a screen shot illustrating a patient's Medical Information screen 914 according to one embodiment. The user may then enter pharmacy 916 and medications 918 into the database. This information is also entered in the appropriate fields. The following is an example of the information that may be entered in the Medical Information Record: 1) Pharmacy 916—Name of patient's pharmacy and phone; 2) Medication 918—Patient's current medication as prescribed by the physician.

To enter the medication(s) in the patient record the user may then enter the medication Name using either the pull-down menu or manual entry. Medications may be permanently added to the pull-down menu by manually entering the medication name and following the instructions in the System. The user may then enter the medication Dose (e.g., 10 mg.) in corresponding dose field 920. Finally, the user may enter the medication frequency in 9×/day (e.g., 2) in the medication frequency field 922.

Figure 10:
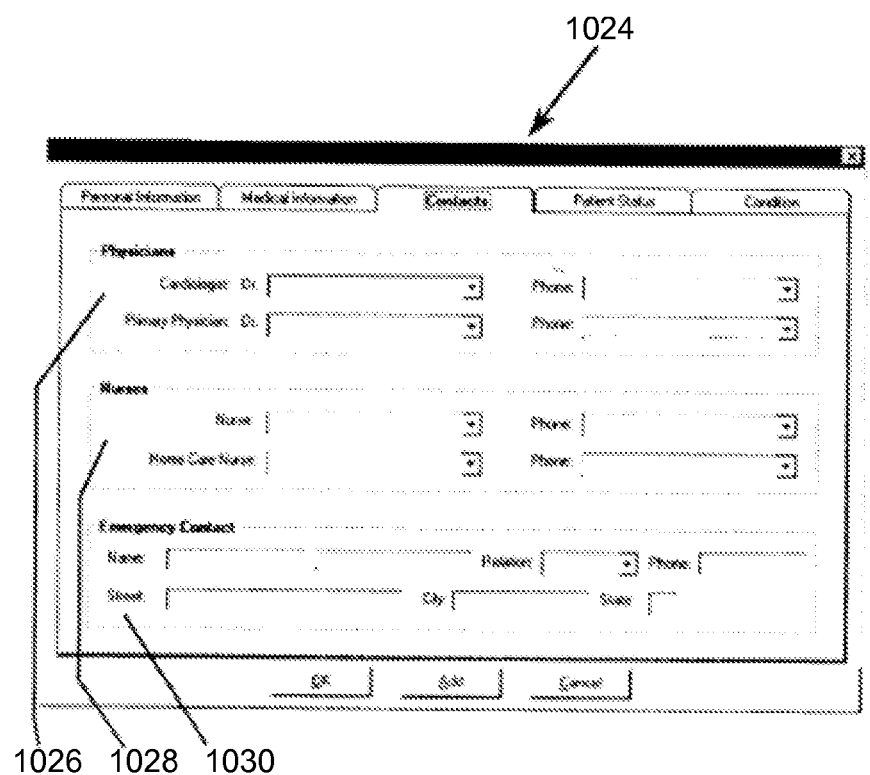
FIG. 10 is a screen shot illustrating a patient's Contact screen according to one embodiment.

FIG. 10 is a screen shot illustrating a patient's Contact screen 1024 according to one embodiment. For example, the user may then enter the patient's physician 1026, nurses 1024 and emergency contacts 1030. This information is also entered in the appropriate fields using either the pull-down menu or manual entry.

Figure 11:
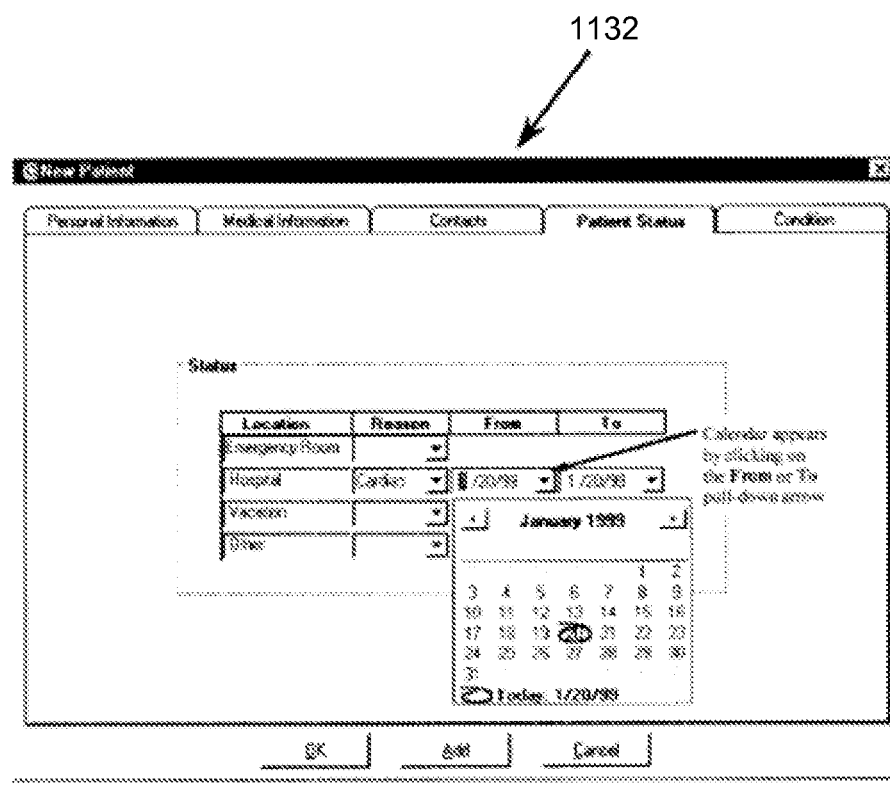
FIG. 11 is a screen shot illustrating a Patient Status screen according to one embodiment.

FIG. 11 is a screen shot illustrating a Patient Status screen 1132 according to one embodiment. This information is also entered in the appropriate fields. However, the Patient Status should be entered only if the patient will not be using the system immediately because he/she is in the Emergency Room, Hospital or on Vacation. The following is an example of how the Patient Status would be entered: 1) Identify the patient's Location; 2) Next to the selected location, enter the Reason by double-clicking on the field, and selecting one of the following: CHF, Cardiac, or Other; 3) Enter the dates the patient will be at the alternative location in the "From" and "To" fields. During this time period, Health Check information will not be reported; 4) The dates can be entered by clicking on the From and To field and using the pull-down menu to view the calendar. Move the mouse pointer to the desired date in the calendar, then click on it. The date will automatically be entered into the From or To field.

Figure 12:
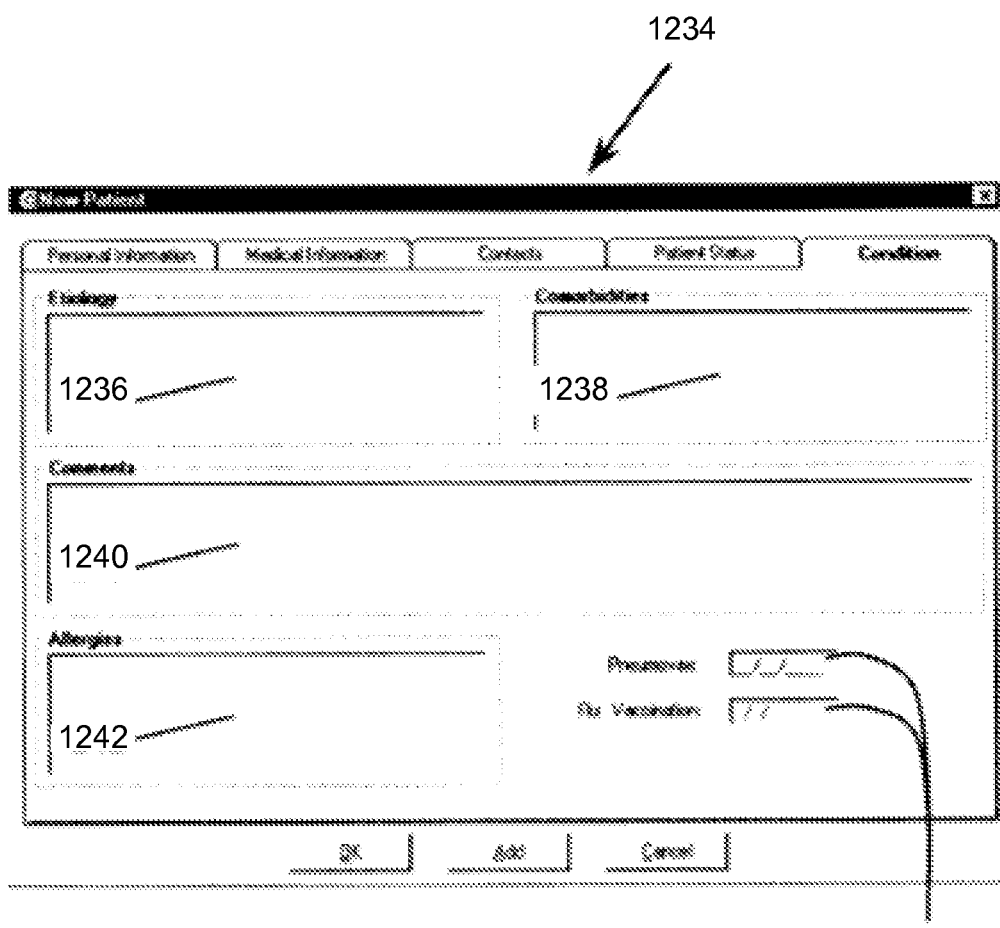
FIG. 12 is a screen shot illustrating a Patient Condition screen according to one embodiment.

FIG. 12 is a screen shot illustrating a Patient Condition screen 1234 according to one embodiment. The screen 1234 may include permanent notes that should be stored in the patient's, record. Permanent fields include: Etiology 1236, Comorbidities 1238, Comments 1240, allergies 1242, and the dates 1244 of the patient's most recent vaccinations. This information is also entered in the appropriate fields.

When finished entering the patient information, the user may either return to the main menu or enter another patient record. Pressing OK enters the patient record into the system database and program execution returns to the main menu. Pressing Add allows the user to enter the patient record into the database and continue entering additional patient records.

Pressing Cancel allows the user return to the main menu. accordingly, no information will be entered.

Figure 13:
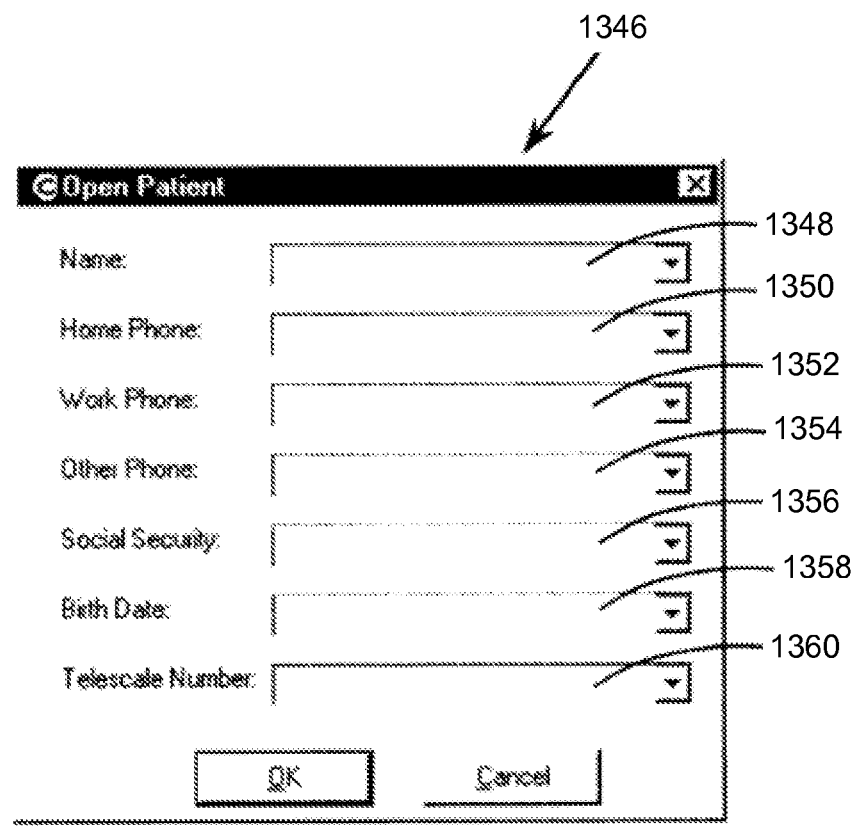
FIG. 13 is a screen shot illustrating a patient record edit screen according to one embodiment.

FIG. 13 is a screen shot illustrating a patient record edit screen 1346 according to one embodiment. The screen 1346 may be displayed in case there may be a need to update or change the information in a patient record the user may edit the database. To edit a Patient record the user may select File, Open, Patient on the menu bar or may click on the appropriate icon. To locate the desired record, the user may begin typing in a field unique to the patient or use the pull-down menus. Searchable fields include: 1) Name (Last, First) 1348; 2) Home Phone 1350; 3) Work Phone 1352; 4) Other Phone 1354; 5) Social Security Number 1356; 6) Birth Date 1358; and 7) TELESCALE™ Number 1360 (Serial Number).

Once the desired record is located, the user may press OK. The Edit Patient screen 1346 will then be displayed and the user may make the necessary changes in the patient record. Pressing OK saves the changes to the patient record. Otherwise, pressing Cancel returns the user to the main menu and no information will be changed.

Figure 14:
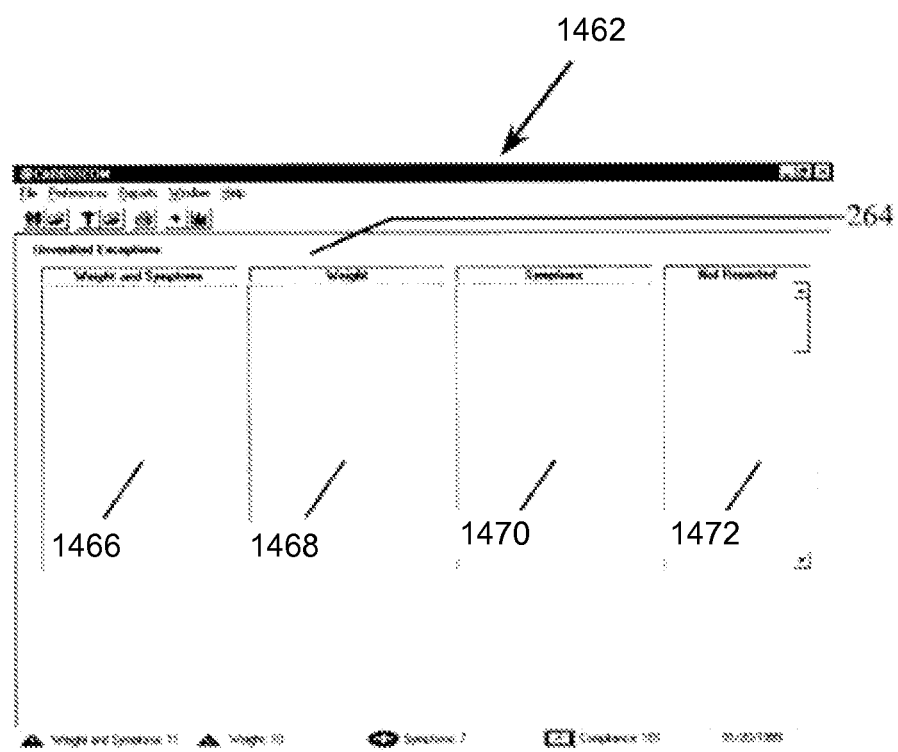
FIG. 14 is a screen shot illustrating a monitoring screen according to one embodiment.

FIG. 14 is a screen shot illustrating a monitoring screen 1462 according to one embodiment. The screen 1462 may allow easy viewing of patients which are categorized based on reported symptoms (the total score of reported symptoms). The user may simply double click on the patient's name and will be taken to the patient's unverified exception record. Monitoring patients includes viewing unverified exception fields 1464 and resolving exceptions. For example, to resolve exceptions, the "Weight and Symptom" exceptions 1466 are verified and "Not Reported" exceptions 1472 are verified.

In one embodiment, patients requiring attention will appear in the Unverified Exceptions screen 1464. These patients have been identified and categorized by: 1) Weight and Symptoms 1466: patient is above their Maximum Allowed Weight+Trigger Weight Change AND has reported symptoms of CHF; 2) Weight 1468: patient is above their Maximum Allowed Weight+Trigger Weight Change; 3) Symptoms 1470: patient has reported symptoms of CHF; and 4) Not Reported 1472: patient has not reported their daily Health Check.

The Unverified Exceptions screen 1462 is the System's main menu and is always displayed. To go to Unverified Exceptions from another screen, the user may select Window, Unverified Exceptions or just click on it in the background. Patients who need to be contacted are listed in one of the following four columns: 1) Weight and Symptoms 1466; 2) Weight 1468; 3) Symptoms 1470; and 4) Not Reported 1472.

Once the System has issued an Exception, in order to resolve the Exception, the medical professional caregiver will need to contact the patient, verify the problem, and notify the physician or health professional as necessary. At the beginning of each day, all patients who have not reported their Health Check will appear in the Not Reported column.

In one embodiment of the invention, to verify a weight and/or symptom exception the user may click on the patient's name in the Unverified Exceptions screen. This will take the user directly to the Exception Verification screen.

Figure 15:
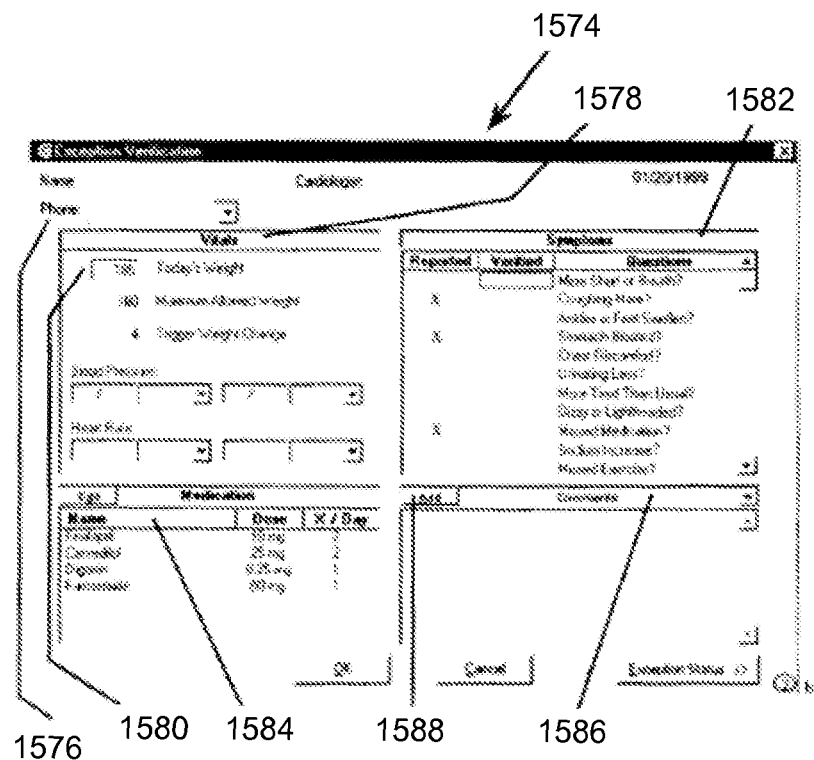
FIG. 15 is a screen shot illustrating an Exception Verification Screen according to one embodiment.

FIG. 15 is a screen shot illustrating an Exception Verification Screen 1574 according to one embodiment. Once at the Exception Verification screen 1574, the user may verify and record the patient's weight, symptoms, and medications.

Subsequently, the user will contact the patient by telephone. The patient's telephone number 1576 is listed in the top left-hand corner under the patient's name. Once the patient has been contacted, the user then goes to the Vitals and Symptoms section 1578 and may verify the information reported in from the patient home monitoring apparatus. The caregiver may verify this data during the review process with the patient.

During the process, the user then goes to the Symptoms section 1582. If the patient has reported a specific symptom, the Reported field adjacent to that question will display an "X" and the question will be highlighted in bold. The user will confirm all of the patient's Health Check answers.

The user then goes to the Medication section 1584. The Medication section 1584 asks the patient if he/she has been taking the medications in the doses and frequencies listed. If the patient has not been taking their medications as specified, the user will state the discrepancy in the Comments section 1586. If the physician has revised the medication regimen, the user will make the appropriate changes by selecting Edit Medications.

The user then goes to the Comments section 1586. The user has the option of adding multiple types of comments for the patient. These comments include: Impression, Nurse Assessment, Plan and Comments. The user may add to the patient's information by clicking the mouse on the Add button 1588. The comment entry window will then appear. The user may then proceed to enter notes in the Nurse Assessment, Comments and Plan boxes. Pressing OK will date stamp and store the notes in the exception report in the database.

The user may view the Comments, Impression, Nurse Assessment or Plan information that was just entered. The user may also view the previous comments by type. The Exception Report is a document that alerts the physician when the patient's reported symptoms and/or weight is outside predetermined limits; or when the patient does not report their daily Health Check. Now the Exception Report is ready to be printed. The Exception Report is stored in the database.

Figure 16:
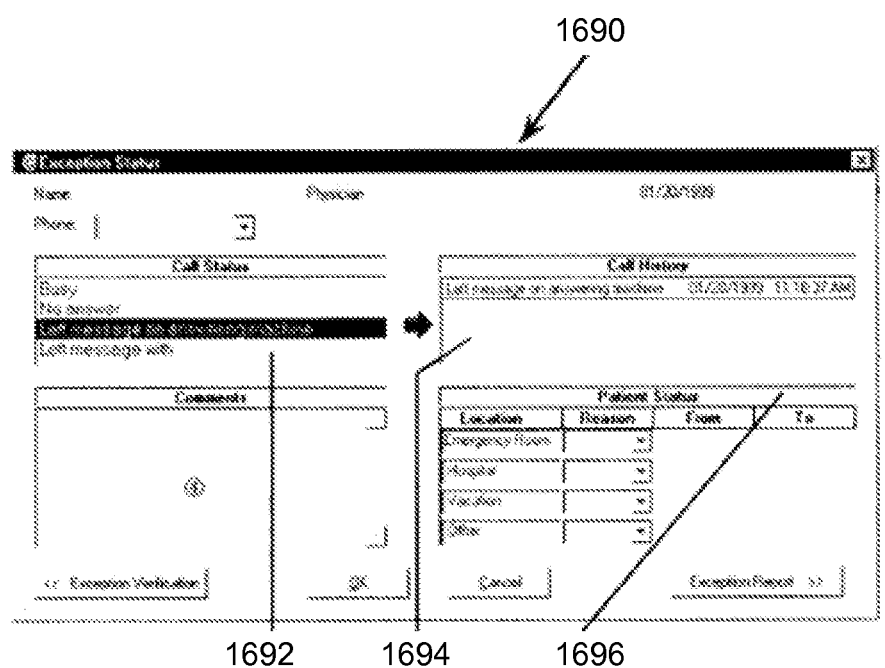
FIG. 16 is a screen shot illustrating an Exception Status Screen according to one embodiment.

FIG. 16 is a screen shot illustrating an Exception Status Screen 1690 according to one embodiment. To verify a Not Reported Exception the user should click on the patient's name in the Unverified Exceptions screen 1662. This will take the user directly to the Exception Status screen 1690. The Exception Status screen 1690 is used to record the user's attempts to contact the patient and the patient's current status. The user must then call the patient at the patient's telephone number listed in the top left-hand corner. If the user is unable to speak with the patient, the user records the reason along with the date and time. In one embodiment of the invention, a double click on one of the following actions in the Call Status section 1692: Busy; No Answer; Left message on answering machine; or Left message with (name of person) will record the information along with date and time in the Call History box 1694.

If the user is able to speak with the patient, the user will ask them why they have not used the patient monitoring device. Accordingly, the user will record the reason in the Comments box. Then, the user should ask the patient to complete the Health Check using the patient monitoring device. Otherwise, the user may verify the patient's weight and symptoms during this phone call by pressing the Exception Verification button on the bottom left side of the screen. Pressing OK, returns the program to the Unverified Exceptions screen. The patient's name will remain in the Not Reported column in the Unverified Exceptions screen until the user is able to obtain the patient's Health Check information. An Exception Report will not be issued.

If there is a change in the patient's status, the user can record this information in the Patient Status section 1696 by choosing one of the following locations: ER (Emergency Room); Hospital; Vacation; or Other. The user should then enter the Reason the patient is unable to use the System by double-clicking on the Reason field and selecting one of the three choices: CHF, Cardiac or Other. The date is then entered in the From box. If no date is entered, the System will automatically enter the current date. The date the patient will be returning is then entered in the "To" box (If you do not enter a date, the System will enter the same date that is in the "From" box.).

In one embodiment, an Exception Report may be a document that alerts the physician or healthcare professional to significant changes that have occurred in a patient's weight and wellness after the reported information has been verified by the user. It is also used to identify patients who have not reported their Health Check. Exception Reports can be viewed on the screen and printed for physician review. The Exception Report may also be transmitted to the emergency service 102 for review during an emergency by first responders.

Computer Systems for Emergency Response

Figure 17:
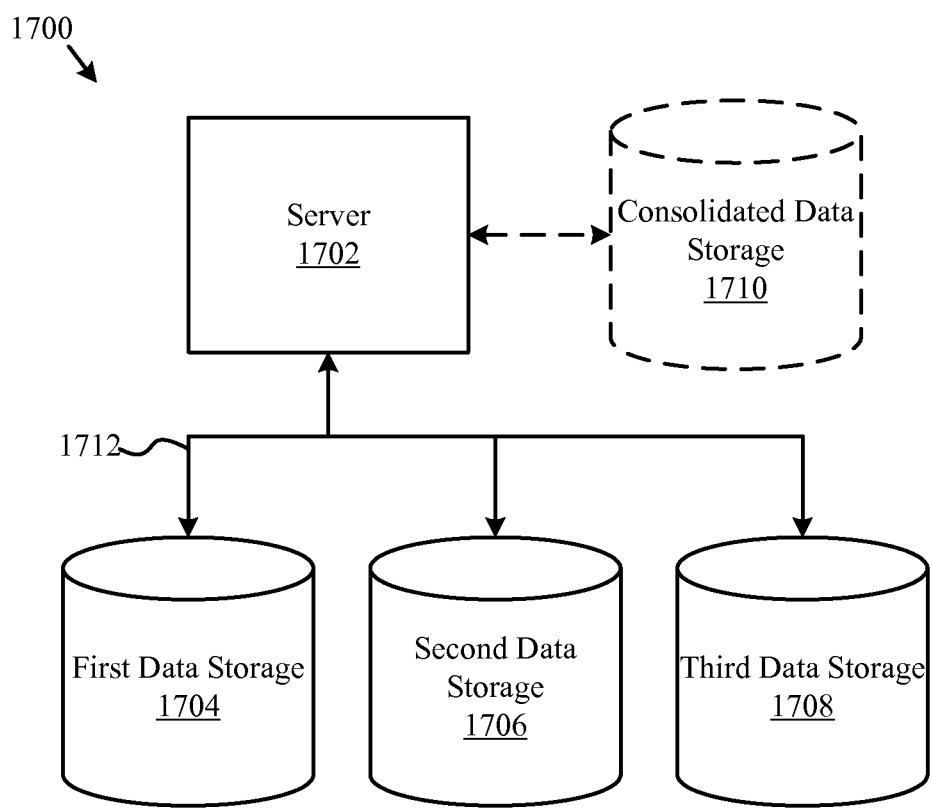
FIG. 17 illustrates one embodiment of a data management system configured to store medical information and personal information.

FIG. 17 illustrates one embodiment of a data management system 1700 configured to store medical information and personal information. In one embodiment, the data management system 1700 may include the server 1702. The server 1702 may be coupled to a data-bus 1712. In one embodiment, the data management system 1700 may also include a first data storage device 1704, a second data storage device 1706, and/or a third data storage device 1708. In further embodiments, the data management system 1700 may include additional data storage devices (not shown). In such an embodiment, each data storage device 1704, 1706, and 1708 may each host a separate database that may, in conjunction with the other databases, contain redundant data. Alternatively, a database may be spread across storage devices 1704, 1706, and 1708 using database partitioning or some other mechanism. Alternatively, the storage devices 1704, 1706, and 1708 may be arranged in a RAID configuration for storing a database or databases through may contain redundant data. Data may be stored in the storage devices 1704, 1706, 1708, 1710 in a database management system (DBMS), a relational database management system (RDMS), an object oriented database management system (OODMS), an Indexed Sequential Access Method (ISAM) database, a Multi Sequential Access Method (MSAM) database, a Conference on Data Systems Languages (CODASYL) database, or other database system.

In one embodiment, the server 1702 may submit a query to select data from the storage devices 1704 and 1706. The server 1702 may store consolidated data sets in a consolidated data storage device 1710. In such an embodiment, the server 1702 may refer back to the consolidated data storage device 1710 to obtain a set of records. Alternatively, the server 1702 may query each of the data storage devices 1704, 1706, and 1708 independently or in a distributed query to obtain the set of data elements. In another alternative embodiment, multiple databases may be stored on a single consolidated data storage device 1710.

In various embodiments, the server 1702 may communicate with the data storage devices 1704, 1706, and 1708 over the data-bus 1712. The data-bus 1712 may comprise a storage area network (SAN), a local area network (LAN), or the like. The communication infrastructure may include Ethernet, fibre-channel arbitrated loop (FC-AL), fibre-channel over Ethernet (FCoE), small computer system interface (SCSI), internet small computer system interface (iSCSI), serial advanced technology attachment (SATA), advanced technology attachment (ATA), cloud attached storage, and/or other similar data communication schemes associated with data storage and communication. For example, the server 1702 may communicate indirectly with the data storage devices 1704, 1706, 1708, and 1710 by first communicating with a storage server (not shown) or the storage controller 1704.

The server 1702 may include modules for interfacing with the data storage devices 1704, 1706, 1708, and 1710, may include modules for interfacing with the network 1708, and/or modules for interfacing with a user through the user interface device 1710. In a further embodiment, the server 1702 may host an engine, application plug-in, or application programming interface (API).

Figure 18:
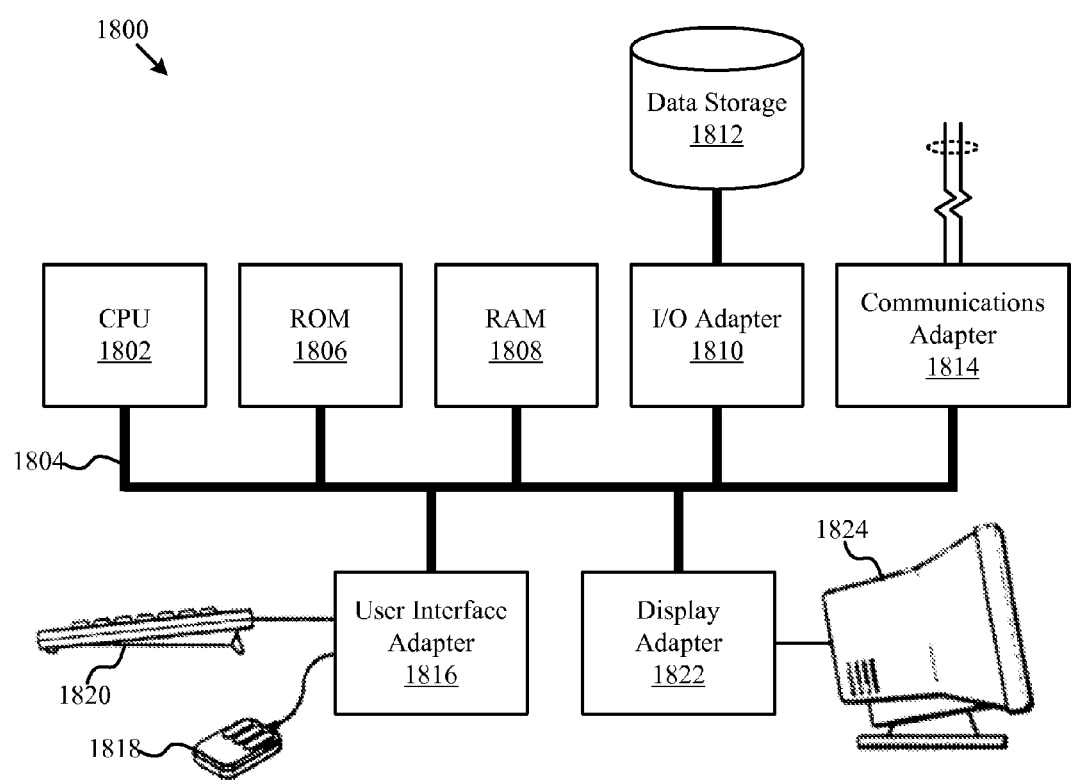
FIG. 18 illustrates a computer system adapted according to certain embodiments of the server or the base receiver.

FIG. 18 illustrates a computer system 1800 adapted according to certain embodiments of the server 1702 of FIG. 17 or the base receiver 108 of FIG. 1. The central processing unit ("CPU") 1802 is coupled to the system bus 1804. The CPU 1802 may be a general purpose CPU or microprocessor, graphics processing unit ("GPU"), and/or microcontroller. The present embodiments are not restricted by the architecture of the CPU 1802 so long as the CPU 1802, whether directly or indirectly, supports the modules and operations as described herein. The CPU 1802 may execute the various logical instructions according to the present embodiments.

The computer system 1800 also may include random access memory (RAM) 1808, which may be synchronous RAM (SRAM), dynamic RAM (DRAM), and/or synchronous dynamic RAM (SDRAM). The computer system 1800 may utilize RAM 1808 to store the various data structures used by a software application such as databases, tables, and/or records. The computer system 1800 may also include read only memory (ROM) 1806 which may be PROM, EPROM, EEPROM, optical storage, or the like. The ROM may store configuration information for booting the computer system 1800. The RAM 1808 and the ROM 1806 hold user and system data.

The computer system 1800 may also include an input/output (I/O) adapter 1810, a communications adapter 1814, a user interface adapter 1816, and a display adapter 1822. The I/O adapter 1810 and/or the user interface adapter 1816 may, in certain embodiments, enable a user to interact with the computer system 1800. In a further embodiment, the display adapter 1822 may display a graphical user interface associated with a software or web-based application on a display device 1824, such as a monitor or touch screen.

The I/O adapter 1810 may couple one or more storage devices 1812, such as one or more of a hard drive, a flash drive, a compact disk (CD) drive, a floppy disk drive, and a tape drive, to the computer system 1800. The communications adapter 1814 may be adapted to couple the computer system 1800 to a network, which may be one or more of a LAN, WAN, and/or the Internet. The communications adapter 1814 may be adapted to couple the computer system 1800 to a storage device 1812. The user interface adapter 1816 couples user input devices, such as a keyboard 1820, a pointing device 1818, and/or a touch screen (not shown) to the computer system 1800. The display adapter 1822 may be driven by the CPU 1802 to control the display on the display device 1824.

The applications of the present disclosure are not limited to the architecture of computer system 1800. Rather the computer system 1800 is provided as an example of one type of computing device that may be adapted to perform the functions of a server 1802 and/or the user interface device 1810. For example, any suitable processor-based device may be utilized including, without limitation, personal data assistants (PDAs), tablet computers, smartphones, computer game consoles, and multi-processor servers. Moreover, the systems and methods of the present disclosure may be implemented on application specific integrated circuits (ASIC), very large scale integrated (VLSI) circuits, or other circuitry. In fact, persons of ordinary skill in the art may utilize any number of suitable structures capable of executing logical operations according to the described embodiments.

If implemented in firmware and/or software, the functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and blu-ray disc, where disks usually reproduce data magnetically, while discs reproduce data optically with lasers. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

The Base Receiver as a Medical Monitoring Station

In one example embodiment, the base receiver 108 of FIG. 1 can be configured as a patient monitoring apparatus for recording medical information, querying personal medical devices for obtaining medical information, and querying one or more individual users to obtain medical information.

Figure 19:
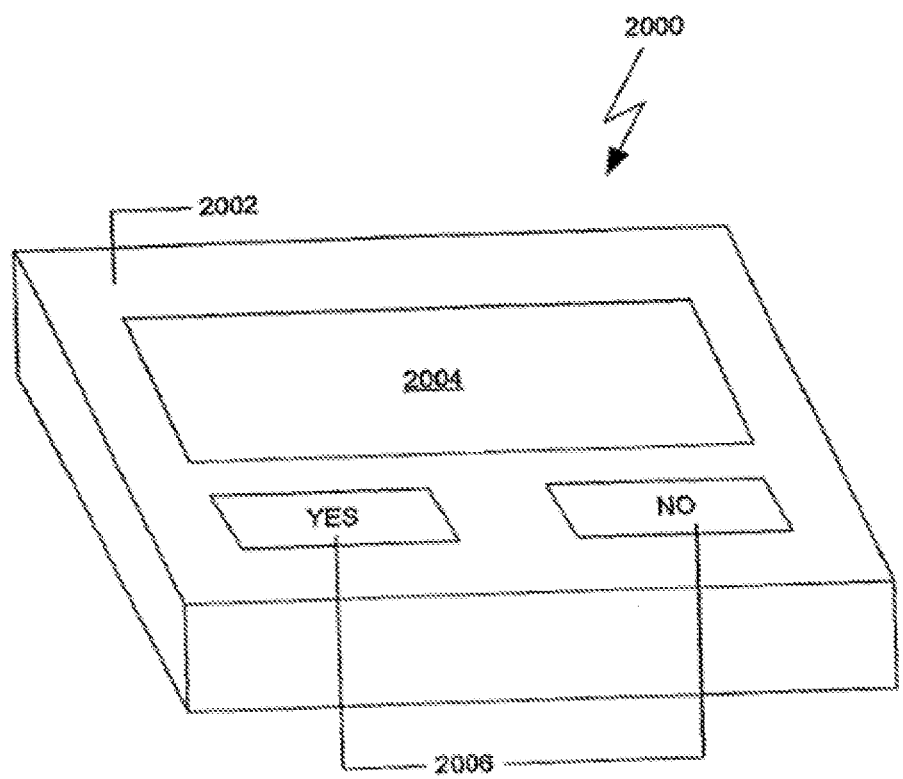
FIG. 19 depicts an embodiment of the present invention, in which a physiological parameter-measuring device is an optional component.

FIG. 19 depicts an embodiment of the patient monitoring apparatus 2000, (which can serve as the base receiver 108 of FIG. 1) in which the housing 2002, the output device 2004, and the input device 2006 stand alone as a complete unit. (A physiological parameter-measuring unit, such as a scale, is not required to interface with the unit 2000, but may be added). As in other embodiments, circuitry for operation of the device is held within the housing 2000. The output device 2002 may be a display, such as an LCD screen, and may include an audio output unit. The input device 2006 is depicted as two buttons, a "YES" button and a "NO" button. One skilled in the art understands that the input device may be a keypad, a mouse, a button, a switch, a light pen, or any other suitable input device. In one embodiment of the invention, the input and output devices 2004 and 2006 are combined into a touch-screen device.

The patient monitoring apparatus 2000 of FIG. 19 may be programmed to contain a plurality of question hierarchies, each of which relates to a health-related symptom. Each hierarchy contains a set of questions. Each question in a given hierarchy is aimed at characterizing a particular symptom in a particular way. Certain questions within a hierarchy may be deemed moot (and thus will not be asked) in light of a patient's answer to a previous question. Details regarding question hierarchies will be discussed in greater detail, below. In one example embodiment, the patient monitoring apparatus 2000 may be programmed by the remote are system, such as the remote care system 110 of FIG. 1. Each time the patient monitoring apparatus 2000 communicates with the remote care system, the remote care system can download new instructions to the patient monitoring apparatus.

By programming the patient monitoring apparatus 2000 to contain a plurality of question hierarchies, the unit 2000 attains great flexibility as a tool for monitoring chronic diseases of many varieties. A particular chronic disease may be monitored by asking questions about symptoms associated with the disease. Thus, for example, the unit 2000 may be made to monitor the health status of a patient with chronic obstructive pulmonary disease (COPD) by querying the patient, using questions extracted from question hierarchies relating to symptoms associated with COPD. The same unit 2000 may be used to monitor a patient with diabetes by asking questions extracted from a different set of question hierarchies, which are related to symptoms associated with diabetes.

Figure 20:
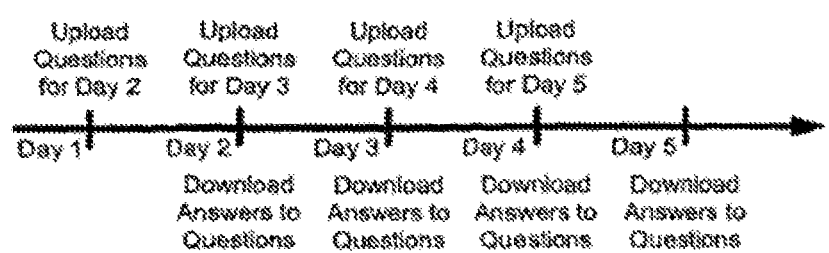
FIG. 20 illustrates a scheme of asking customized questions and collecting the answers thereto.

FIG. 20 illustrates a scheme of asking customized questions and collecting the answers thereto. As can be seen from FIG. 20, a set of customized questions may be downloaded to a monitoring device 1100 on DAY N from a remote care center, such as the remote care center 110 of FIG. 1. The customized questions will be asked to the patient 1105, and the answers recorded either later in the day on DAY N or on DAY N+1 (depending upon the particular 2-way scheme employed). The answers to the customized questions are retrieved by the central computer 1102 on DAY N+1. The particular questions asked from day-to-day may vary, based upon instruction from the health care provider.

Figure 21:
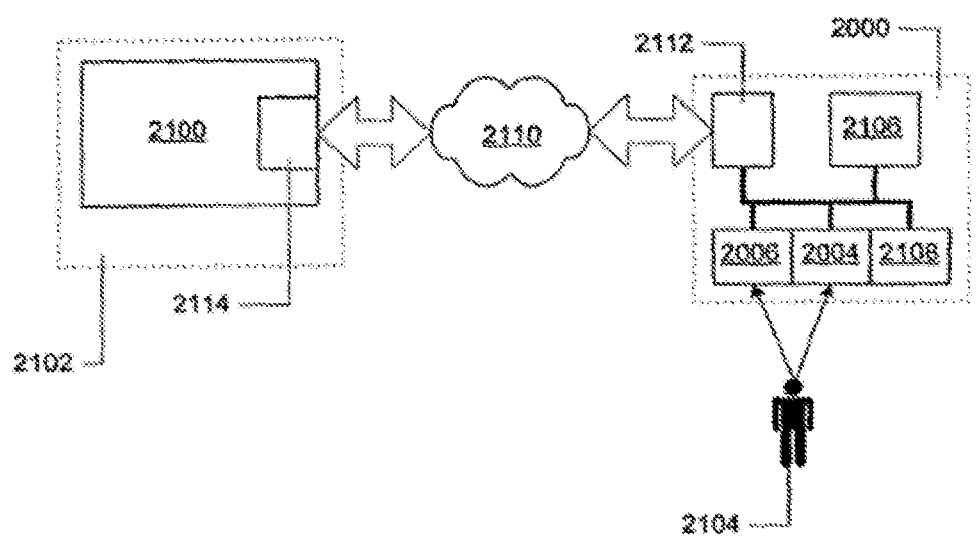
FIG. 21 depicts an embodiment of a system, in which a physiological parameter-measuring device is an optional component.

FIG. 21 is a high-level depiction of a monitoring system employing the embodiment 2000 depicted in FIG. 20, and may be used as a starting point for a more detailed discussion of the patient monitoring apparatus 2000.

As can be seen from FIG. 21, the system comprises a patient monitoring apparatus 2000 and a central computer 2100. The central computer 2100 is housed within a facility 2102 that is located remote from the patient monitoring apparatus 2000. For example, the patient monitoring apparatus 2000 may be located in the home of an ambulatory patient 2104, while the central computer 2100 is located in a health care facility 2102.

As described previously, the patient monitoring apparatus 2000 is composed of a central processor unit 2106, which is in communication with an input device 2006, an output device 2004, and a memory device 2108. The memory device 2108 has a plurality of question hierarchies stored within it, as discussed more fully, below.

As discussed previously, the output device 2004 may be used to prompt the patient 2104 with questions regarding the patient's wellness. The output device 2004 may consist of a visual display unit that displays the questions in a language of the patient's 2104 choosing. Alternatively, the output device 2004 may consist of an audio output unit that vocalizes the questions. In one embodiment, the audio output unit 2004 may vocalize the questions in a language of the patient's 2104 choosing.

The patient monitoring apparatus 2000 communicates with the central computer 2100, such as the remote care system 110, via a network 2110; the patient monitoring apparatus 2000 uses a communication device 2112 to modulate/demodulate a carrier signal for transmission via the network 2110, while the central computer uses a communication device 2114 for the same purpose. Examples of suitable communication devices 2112 and 2114 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network. A system composed as described above may be programmed to carry on periodic (e.g., daily) questioning of a patient 2104, with respect to the patient's 2104 perception regarding his or her own status vis-a-vis a particular set of symptoms. For example, a patient suffering from COPD is likely to experience shortness of breath, both during the day and during the night (amongst many other symptoms). Thus, the system may question the patient 2104 about his own perceptions regarding his shortness of breath. The questions used to determine the patient's 2104 judgment about his own shortness of breath during the day are contained in a first question hierarchy. Similarly, questions related to the patient's 2104 shortness of breath during the night are contained in a second question hierarchy. The first hierarchy, which is related to shortness of breath during the day, may be structured as follows:

TABLE 5

Question Hierarchy: Shortness of Breath During the Day

| | |
|---|---|
| Question #1 | Are you feeling more short of breath? |
| Question #2 | Do you feel more short of breath in response to physical exertion? |
| Question #3 | Do you feel more short of breath during periods of rest? |
| Question #4 | Does stress make you feel more short of breath? |

Each of the questions in the hierarchy is related to day-time shortness of breath. The first question is broadly focused, simply asking "Are you feeling more short of breath?" Clearly, if the patient 2104 were to answer "no" to such a question, the remainder of the questions would be unnecessary. Thus, the system may be designed to prevent the remaining questions from being asked (this will be discussed in greater detail, below). Question #2 asks a question that is more particularized than question #1: "Do you feel more short of breath in response to physical exertion?" An affirmative answer to this question is more serious, and provides more particularized information, than an affirmative answer to the broader query presented in question #1. Although not essential, each question hierarchy may be constructed in accordance with this paradigm: (1) a negative answer to a preceding questions negates the need to ask any additional questions in the hierarchy; (2) successive questions relate to increasingly more particularized aspects of a given symptom; and (3) successive questions relate to an increasing severity level of a given symptom.

Figure 22:
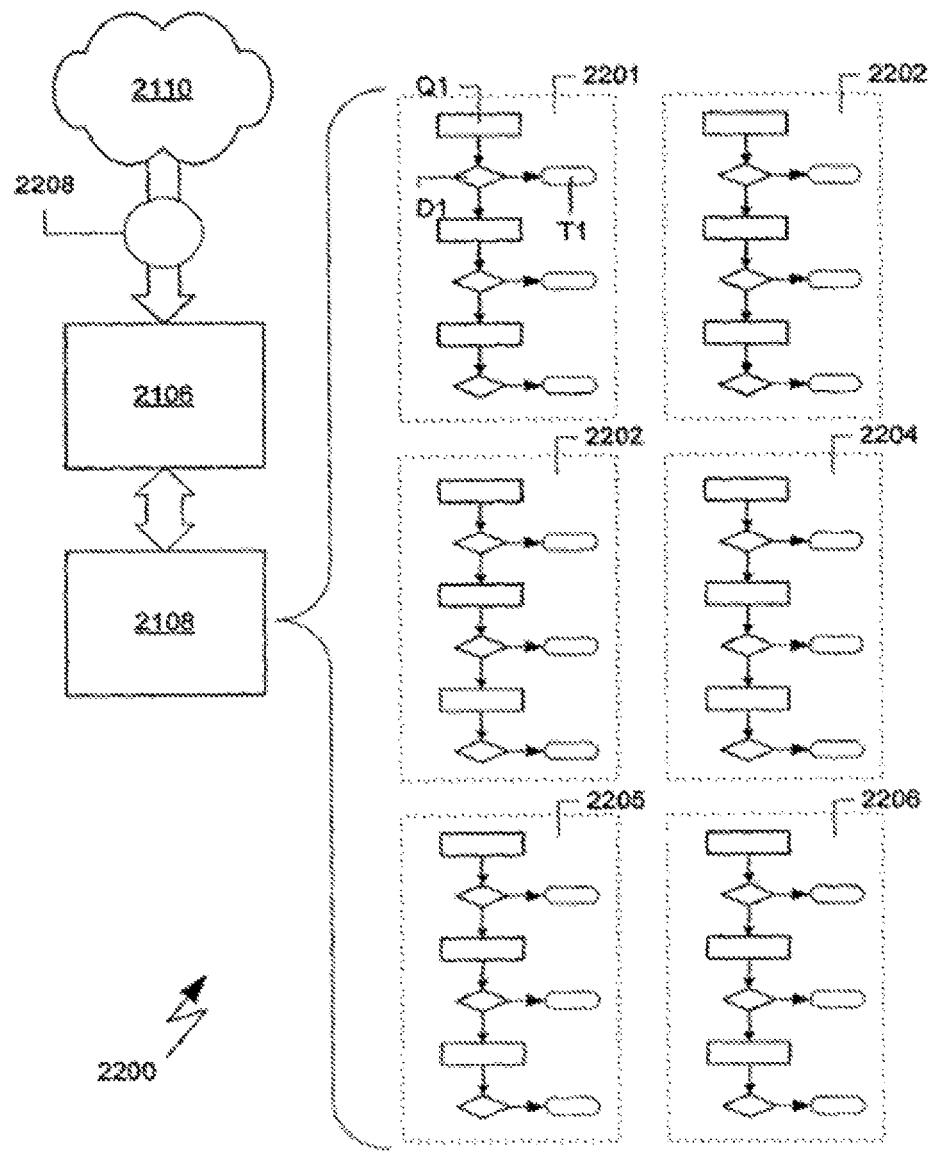
FIG. 22 depicts a memory device programmed with a set of question hierarchies.

FIG. 22 depicts the partial contents of the memory device 2108 of FIG. 21. As can be seen from FIG. 21, the memory device 2108 is programmed with a set of question hierarchies 2200. In the example depicted in FIG. 22, the memory device is programmed with six question hierarchies 2201, 2202, 2203, 2204, 2205, and 2206 (collectively referred to as "the set of question hierarchies 2200"). As described previously, each hierarchy relates to a symptom condition to be monitored, meaning that the number of question hierarchies stored in the memory device 2108 is dependent upon the number of symptoms to be monitored. Hierarchy 2201 has a basic structure that includes a first question Q1, followed by a first decision point D1. At decision point D1, the patient monitoring apparatus 2000 decides whether or not to ask the subsequent question, Q2. For example, Q1 may be a question that reads "Are you feeling more short of breath?" If the patient 2104 answers "no," this answer is analyzed at decision point D1, and the questioning terminates at terminal point T1. Otherwise, the questioning continues with the next question, Q2, and the process continues.

Each of the hierarchies 2200 depicted in FIG. 22 possesses the above-recited structure, although other structures are possible, some of which are described below. One skilled in the art understands that although each hierarchy 2200 is depicted as consisting of three questions, a hierarchy may consist of any number of questions, including a single question.

As depicted in FIG. 22, the memory device 2108 is in data communication with the monitoring device's 2000 microprocessor 2106, which, in turn, is in data communication with a remote computer 2100 (not depicted in FIG. 22) via a network 2110 and via a communication device 2112 (also not depicted in FIG. 22). The remote computer 2100 transmits a symptom identifier 2208 to the monitoring device's 2000 microprocessor 2106. The symptom identifier 2208 corresponds to a question hierarchy 2200. For example, a symptom identifier with a value of "1" may correspond to hierarchy 2201, while a symptom identifier with a value of "2" corresponds to hierarchy 2202, etc. The microprocessor 2106 responds to having received a symptom identifier 2202 by executing the corresponding hierarchy (i.e., asking a question within the hierarchy, and deciding whether or not to ask a subsequent question therein). Thus, the patient monitoring device 2200 may be made to execute n number of question hierarchies by transmitting to it n number of symptom identifiers.

Given that a known set of symptoms are correlated with any given chronic disease, the patient monitoring device 2000 may be tailored to monitor the health status of a patient 2104 with a particular disease by executing question hierarchies 2200 relating to symptoms corresponding with the patient's 2104 particular disease. Thus, the remote computer 2100 may be programmed with software that presents a menu for each patient 2104. The menu allows the health care provider to select from among a set of chronic diseases. Based upon the selected chronic disease, the remote computer 2100 transmits one or more symptom identifiers (which correspond to symptoms known to accompany the selected disease) to the patient monitoring apparatus 2000. The remote computer 2100 receives the patient's 2104 responses, and scores the response in accordance with a scoring algorithm, discussed in detail below. Based upon the outcome of the score, an exception report may be generated, meaning that a health care provider will be notified of the patient's possible need for assistance. Alternatively, the remote computer 2100 may be programmed to transmit an e-mail message or a numeric page to communicate the information concerning the patient 2104. In principle, any data transmission communicating the patient's 2104 potential need for assistance may be transmitted. In certain situations, it may be desirable for the patient monitoring device 2000 to obtain information regarding a physiological parameter. For example, if a particular chronic disease is associated with a fever, the patient monitoring device may want to know information concerning the patient's 2104 body temperature. Two general approaches exist for gaining information concerning a physiological parameter. The monitoring system 2000 may be adapted for interfacing with a physiological parameter-measuring unit, as has been disclosed with reference to other embodiments of the invention. The parameter-measuring unit can then directly measure the physiological parameter and transmit the data to the central computer 2100. Many times, this is an appropriate approach. Accordingly, according to one embodiment of the invention, the microprocessor 2106 may interface with a physiological parameter-measuring device, such as a scale or a thermometer, as previously described herein. On the other hand, oftentimes it is possible to ask the patient to measure the parameter for himself (e.g., take his own temperature). This approach has an advantage, in that the cost of obtaining the information is minimized. This approach is particularly useful when an exact measurement of a physiological parameter is not as useful as simply knowing whether the parameter crosses some threshold. Under these circumstances, the cost of directly obtaining precise information may outweigh the financial benefit of knowing such information. Thus, as depicted in FIG. 23, a question hierarchy 2200 may be designed to ask a patient whether one of his physiological parameters exceeds a threshold, T.

Figure 23:
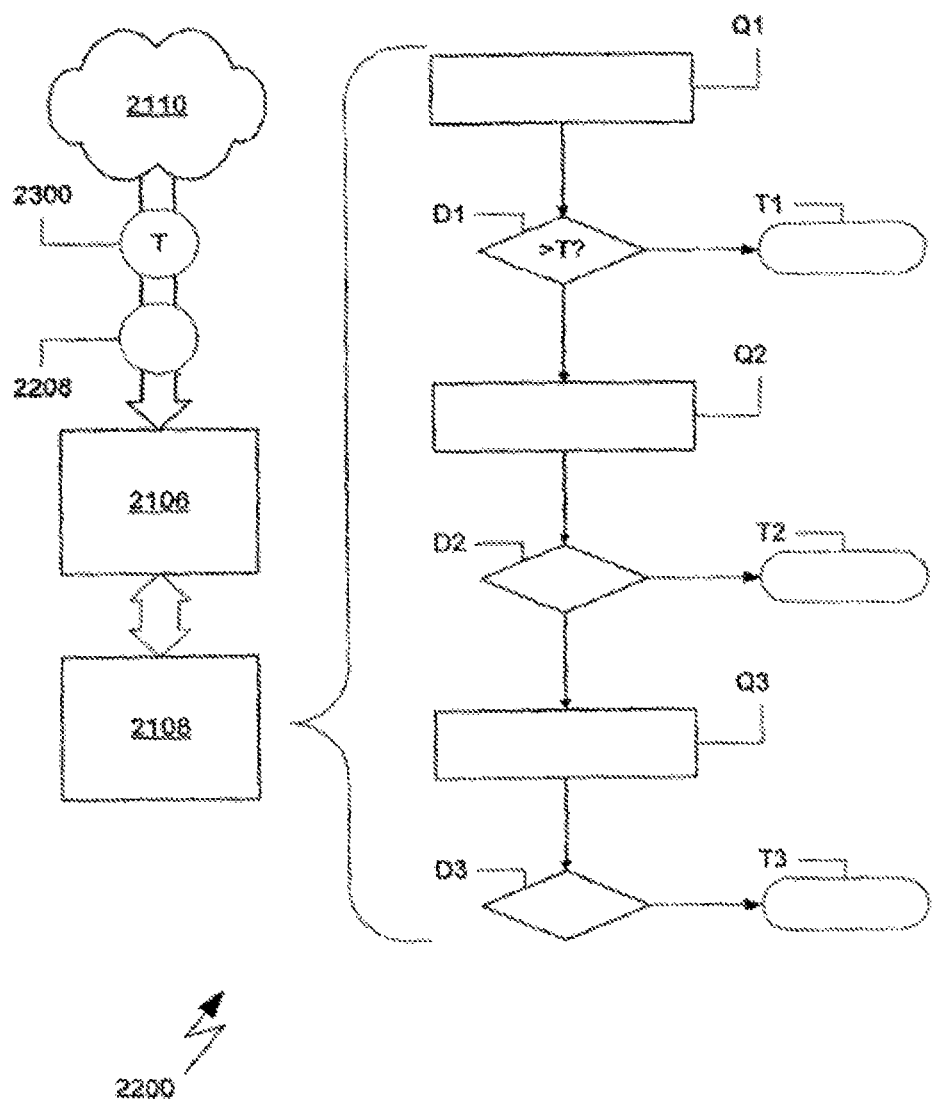
FIG. 23 depicts a particular question hierarchy logical structure, according to one embodiment.

The question hierarchy 2200 depicted in FIG. 23 is similar to the question hierarchies 2200 discussed with reference to FIG. 22. The question hierarchy 2200 corresponds to a symptom identifier 2208, which is transmitted to the patient monitoring device 2000 by a remote computer 2100. The hierarchy 2200 possesses several questions Q1, Q2, and Q3, some of which may go unasked, if a decision point D1, D2, or D3 terminates the flow of questioning by transferring execution flow to a terminal point T1, T2 or T3. Of particular note in the question hierarchy 2200 of FIG. 23 is the first question, Q1, and the first decision point D1. The first question, Q1, asks the patient 2104 if a particular physiological parameter of his exceeds a given threshold, T. The value represented by T is transmitted to the patient monitoring device 2000 by the remote computer 2100, as is depicted by threshold datum 2300. Therefore, to invoke this particular hierarchy 2200, the remote computer should transmit both a symptom identifier 2208 and a threshold datum 2300. In response, the patient monitoring device 2000 responds by asking the patient 2104 if his particular physiological parameter exceeds the threshold, T. Next, as is depicted by decision point D1, the patient monitoring device 2000 determines whether or not to proceed with further questions, on the basis of whether or not the parameter exceeded the threshold, T.

Figure 24:
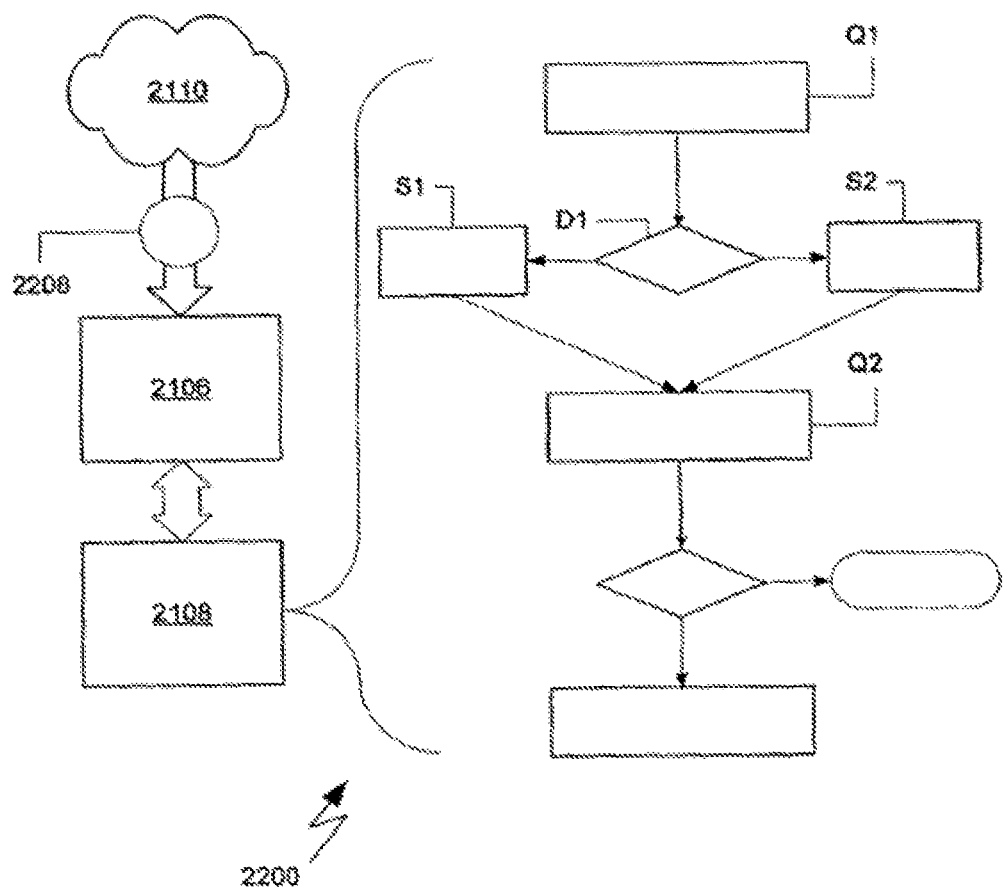
FIG. 24 depicts another question hierarchy logical structure, according to one embodiment.

Another situation likely to arise in the context of monitoring a patient 2104 with a chronic illness is that the patient 2104 is to be queried regarding his faithfulness to a prescribed health care regimen. For example, if the patient 2104 is a diabetic, the patient is likely to be on a strict diet. The patient monitoring device 2000 may be programmed to ask the patient 2104 if he has been following his diet. If the patient 2104 answers "yes," the device 2000 may respond by praising the patient 2104—a tactic that may be particularly advantageous for young patients. On the other hand, if the patient 2104 answers "no," the device 2000 may respond by ■ reminding the patient 2104 to adhere to his diet. FIG. 24 depicts a question hierarchy 2200 designed to achieve the results of praising a patient 2104 for adhering to a prescribed regimen, or reminding the patient 2104 of the importance of adhering thereto. Of particular note in the question hierarchy 2200 depicted in FIG. 24 is the first question, Q1. The first question, Q1, asks the patient 2104 if he has been adhering to a health care regimen (such as, a diet or a medication regimen). Next, at decision point D1, flow of execution is adjusted based upon whether or not the patient 2104 has been adhering to the regimen. If the patient 2104 has been adhering to the regimen, the patient 2104 is presented with a statement, S1, praising the patient. Otherwise, the patient 2104 is presented with a statement, S2, reminding the patient 2104 to adhere to his regimen. In either event, execution flow is passed to the second question, Q2, and hierarchy" execution continues in accordance with the flow described with reference to FIG. 22.

Figure 25:
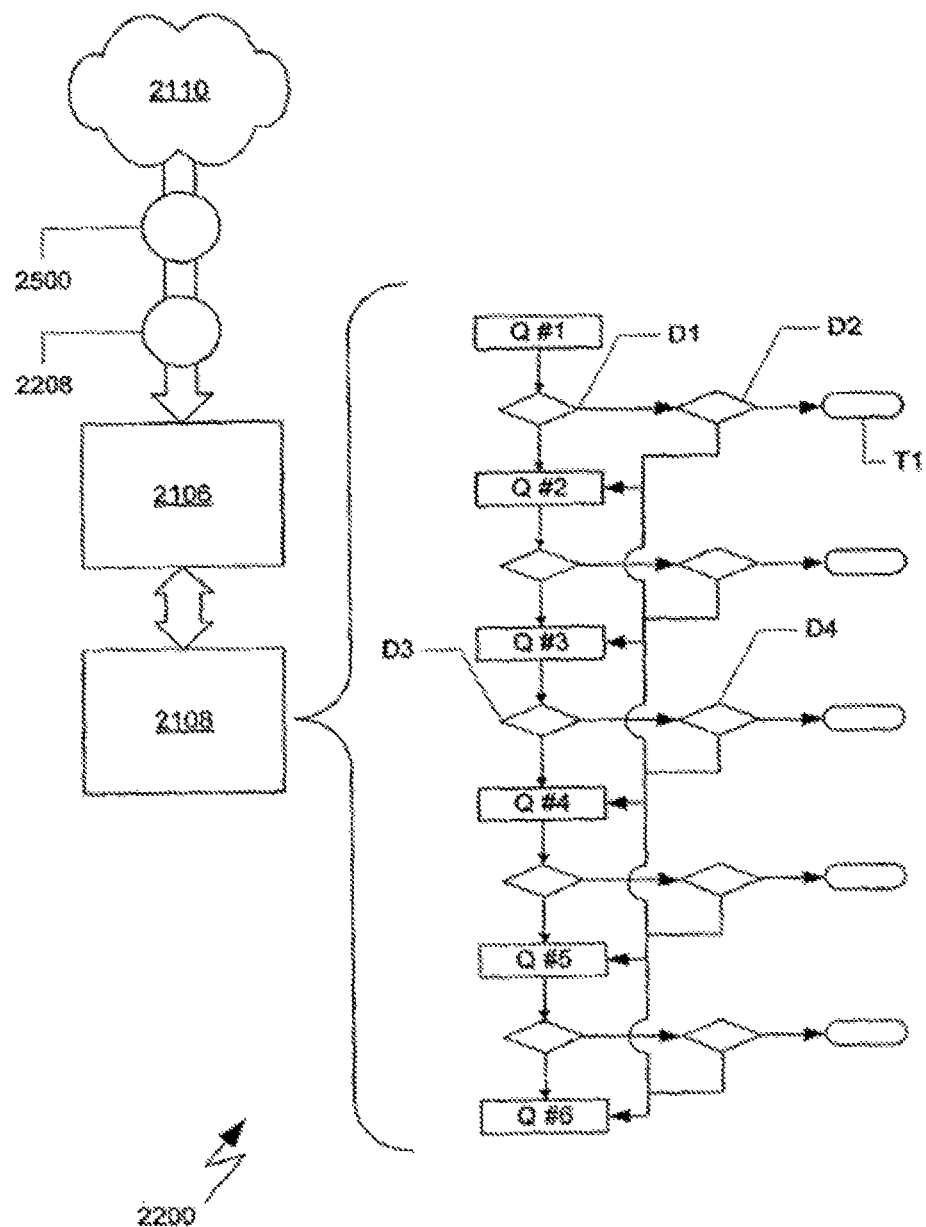
FIG. 25 depicts another question hierarchy logical structure, according to one embodiment.

FIG. 25 depicts a question hierarchy 2200 that has been modified to permit the remote computer 2100 to command specific questions within the hierarchy 2200 to be asked, regardless of any answer that may have been previously given by the patient 2104. To achieve this result, the remote computer 2100 should transmit a symptom identifier 220S corresponding to the question hierarchy 2200. Additionally, a question set 2500 should be transmitted. The question set 2500 may define a set of questions to be forced "on." For example, the question set 2500 may be {3, 5}, meaning that questions 3 and 5 are to be asked, no matter what the patient 2104 has previously answered.

Continuing the discussion assuming that a question set 2500 of {3, 5} had been transmitted, execution of the hierarchy commences with the asking of the first question, Q1. Next, at decision point D1, the patient's 2104 answer to the first question is assessed to determine whether the subsequent question in the hierarchy should be asked. If the answer is such that ordinarily none of the remaining questions should be asked, execution would typically flow to terminal point T1. However, in this embodiment, a second decision point, D2, is interposed between decision point D1 and terminal point T1. At the second decision point, D2, it is determined whether the question set 2500 contains a question number that is higher than the question number that was just asked. In the case of the present example, the question set 2500 contains two such question numbers, because question numbers 3 and 5 are higher than the present question number, 1. If the question set 2500 does contain a question number that is higher than the question number just asked, then execution flows to the smallest such question number (in this case, question number 3, Q3). Thereafter the process repeats, thereby ensuring that each of the question numbers in the question set will be asked.

Figure 26:
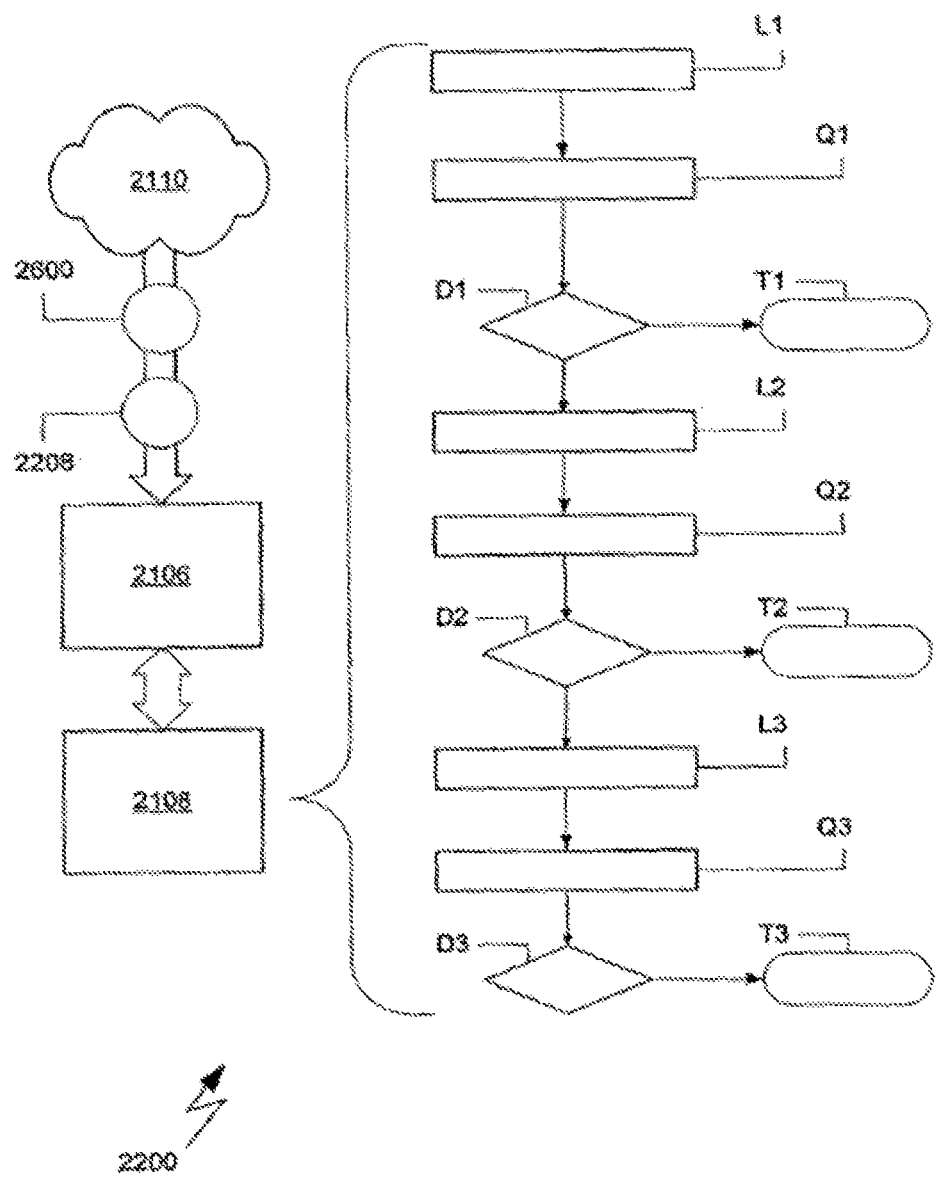
FIG. 26 depicts yet another question hierarchy logical structure, according to one embodiment.

FIG. 26 depicts a question hierarchy 2200 that has been modified to permit the remote computer 2100 to command a specific sequence in which the questions within the hierarchy 2200 should be asked. To achieve this result, the remote computer 2100 should transmit a symptom identifier 2208 corresponding to the question hierarchy 2200. Additionally, a sequence set 2600 should be transmitted. The sequence set 2600 is a set of data defining the order in which the questions are to be asked. For example, the sequence set 2600 may be {3, 1, 2}, meaning that the question that would ordinarily be asked third should be asked first, that the question that would ordinarily be asked first should be asked second, and that the question that would ordinarily be asked second should be asked third.

Continuing on with the example, execution of the hierarchy 2200 of FIG. 26 commences with a look-up operation, L1. During the look-up operation L1, the first element of the sequence set 2600 is used to index into an array containing the questions within the hierarchy. In the present example, since "3" is the first element of the sequence set, the third question from the array is retrieved. Next, the retrieved question (identified as Q1 in FIG. 26) is asked, and execution of the hierarchy proceeds as has been generally described with reference to FIG. 22. Thus, by inserting a look-up operation L1, L2, or L3 prior to each questioning operation Q1, Q2, or Q3, any desired sequence of questioning may be commanded.

The question hierarchies disclosed in FIGS. 22-26 may be programmed into the memory device 2108 of the patient monitoring device 2000, thereby obviating the need to transmit the text of the questions from the central computer 2100 to the patient monitoring device 2000. One skilled in the art understands that the question hierarchies 2200 may be implemented in the form of an application-specific integrated circuit, as well. Optionally, the questions within the hierarchies 2200 may written to be answered with either a "yes" or "no," achieving the advantage of simplifying the input required from the patient 2104, and thereby necessitating only "yes" or "no" buttons for the input device 2006. Further, any of the preceding question hierarchies 2200 forms may be combined.

As described earlier, the memory device 2108 may store each of the question hierarchies 2200 in a plurality of languages, so as to permit patients 2104 of many nationalities to use the device 2000. If the output device 2004 is an audio output unit, the questions within each of the question hierarchies 2200 maybe stored in a digital audio format in the memory device 2108. Accordingly, the questions are presented to the patient 2104 as a spoken interrogatory, in the language of the patient's 2104 choice.

Figure 27:
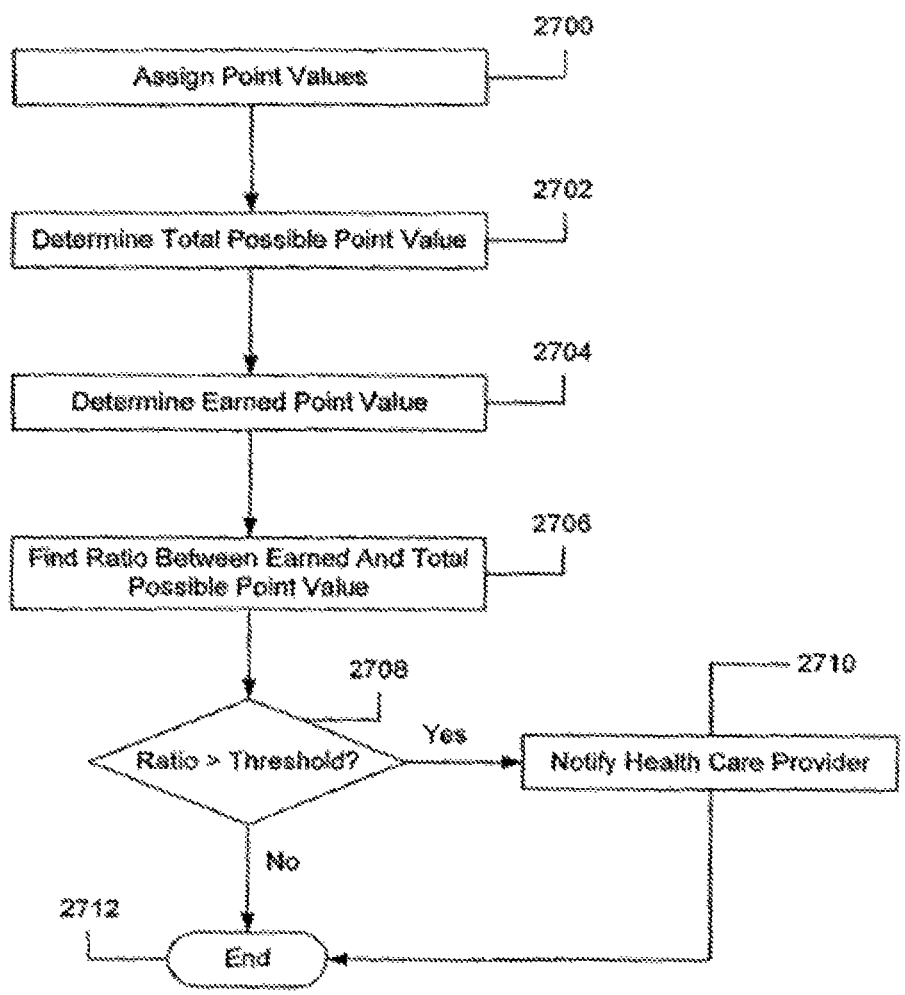
FIG. 27 depicts one method, of determining whether a patient is in need of medical assistance, based upon the patient's response to questions presented from a question hierarchy.

FIG. 27 depicts a method by which the patient's 2104 answers to the questions presented in the hierarchies 2200 may be analyzed along with physiological information. As mentioned earlier, depending upon the outcome of the analysis, an exception report may be issued and a health care provider may be notified. An exception would notify a care giver that follow-up with the patient is required. According to one example method depicted in FIG. 27, during operation 2700 a point value is assigned to each question in each of the invoked question hierarchies 2200. The points assigned to a given question are "earned" by a patient 2104, if the patient answers the question in a particular way. Otherwise, no points are earned. For example, an affirmative response to the question "are you experiencing shortness of breath?" maybe worth 10 points, while a negative response to that question is worth nothing. A standard point value may be assigned to each question (each question has a point value of 10, for instance), or different questions may be assigned different point values (a first question is worth 10 points, while a question directed toward a more serious issue may be worth 30 points, for example). A default point assignment scheme may be presented for approval by a health care provider. The health care provider may then adjust the point assignment scheme to fit the needs of an individual patient 2104.

In operation 2702, the point value of each of the questions actually asked to the patient 2104 is determined. Thus, questions that were not asked to a patient 2104 are not included in this point total. In operation 2704, the patient's 2104 earned point value is totaled. Then, in operation 2706, the patient's 2104 earned point total (determined in operation 2704) is divided by the total possible point value (determined in operation 2702).

In operation 2708, it is determined whether the fraction found in operation 2706 exceeds a threshold (as with the point assignment scheme, the threshold may be defined by the health care provider). If so, the patient's health care provider is notified (perhaps by the issuance of an exception report), as shown in operation 2710. Finally, the process terminates in operation 2712.

Figure 28:
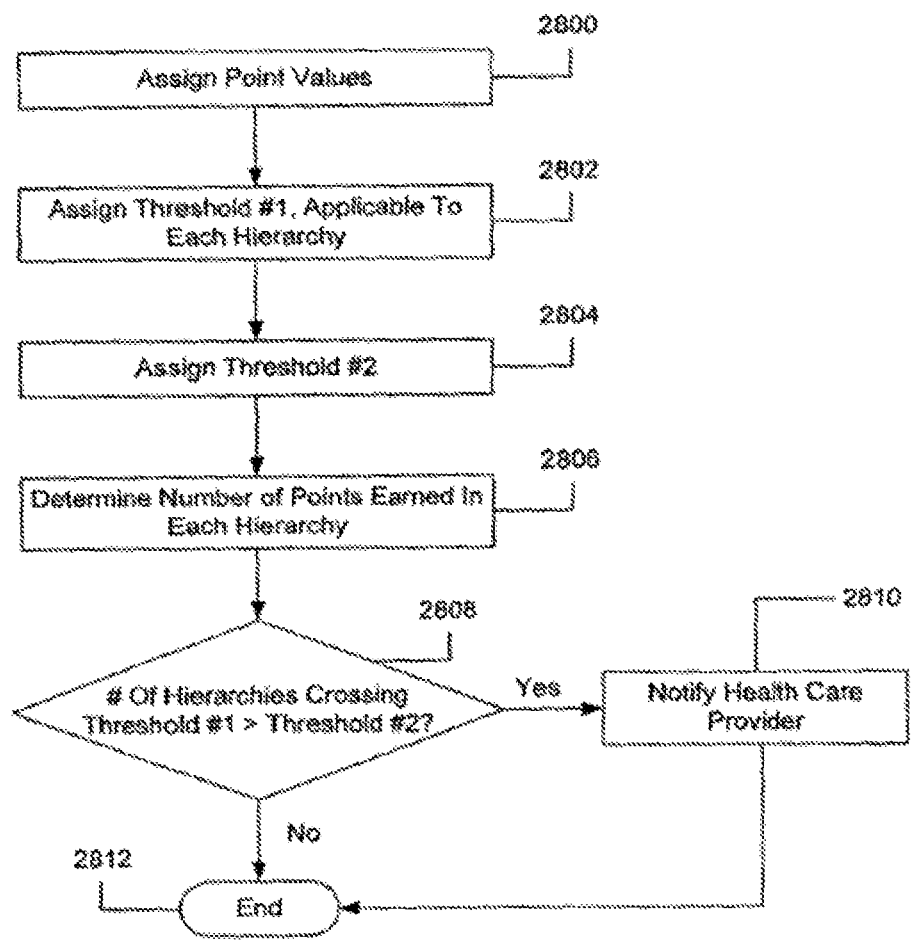
FIG. 28 depicts another method of determining whether a patient is in need of medical assistance, based upon the patient's response to questions presented from a question hierarchy.

FIG. 28 depicts another method by which the patient's 2104 answers to the questions presented in the hierarchies 2200 may be analyzed. According to the method depicted in FIG. 28, during operation 2800 a point value is assigned to each question in each of the invoked question hierarchies 2200. The details of the point assignment scheme are identical to those in operation 2700 of FIG. 27.

Next, in operation 2802, a threshold is assigned to each invoked hierarchy 2200. Again, this threshold may be assigned by default, and the health care provider may be given an option to adjust this threshold. The threshold of operation 2802 applies to each hierarchy 2200, meaning that a decision will be made, on a hierarchy-by-hierarchy basis, whether the patient 2104 has accumulated sufficient points in a particular hierarchy to cross a threshold assigned to that hierarchy 2200. In operation 2804, a second threshold is assigned. The threshold of operation 2804 relates to the number of hierarchies 2200 that may be allowed to exceed the threshold of operation 2802.

In operation 2806, the number of points earned by the patient 2104 in each hierarchy 2200 is determined. Then in operation 2808, it is determined whether the number of hierarchies 2200 in which the threshold of operation 2802 was crossed exceeds the threshold of operation 2804. If so, the patient's health care provider is notified, as shown in operation 2810. Finally, the process terminates in operation 2812.

The methods of FIGS. 27 and 28 are preferably performed by the remote computer 2100, although they may be performed by any other processing device. The aforementioned methods are preferably embodied as software stored in a memory device within the central computer 2100. However, they may be embodied on a computer-readable medium, such as a compact disc, a floppy disc, a network cable, or any other form of media readable by a computer.

Figure 29:
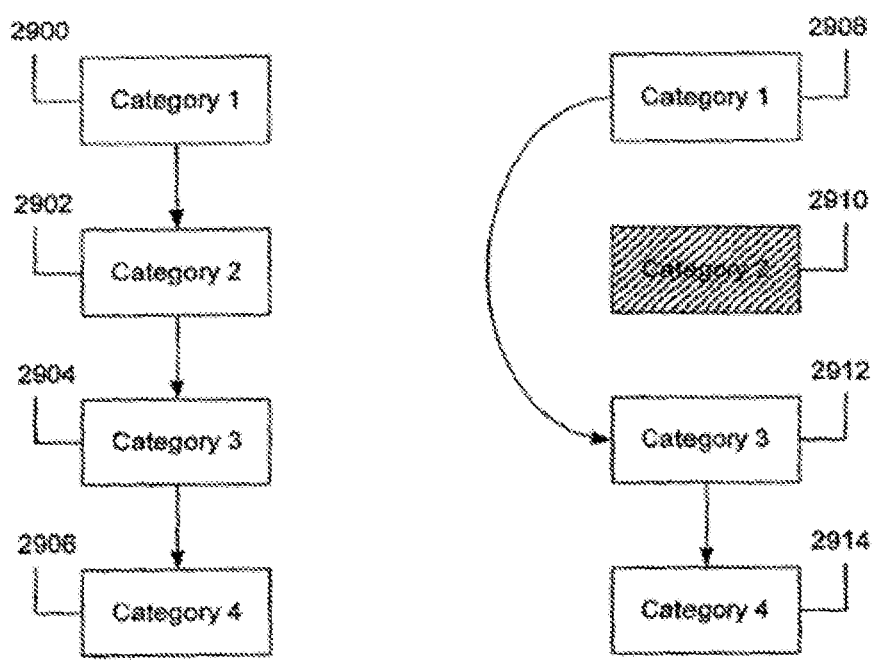
FIG. 29 depicts a questioning scheme according to one embodiment.

FIG. 29 depicts a questioning scheme that may be employed by any of the embodiments of the system depicted or referred to in any of the twenty-eight preceding FIGUREs. As can be seen from FIG. 29 there is shown a first sequence of questions which have been organized into categories 2900, 2902, 2904, and 2906 and a second sequence of questions which have been organized into categories 2908, 2910, 2912, and 2914. Typically, all of the questions within a category such as category 2900 relate to a given topic. In the case of a system for weight loss or weight management, for example, the category may relate to overeating, and each of the questions may related to different facets of overeating.

As shown in FIG. 29, the typical flow for such a scheme is for the questions within a first category, such as category 1 2900, to be asked followed by the questions within a second category, such as category 2 2902, to be asked. Following this, the questions in category 3 2904 are asked, and finally the questions in category 4 2906 are asked. Of course, in principle, a questioning scheme may have questions organized into any number of categories not simply four as is shown in FIG. 29. Further, it is not necessary that the categories be preceded through in sequential fashion, although this is has been shown in FIG. 29. As shown by the question sequence composed of categories 2908, 2910, 2912, and 2914, a given category of questions may be deactivated. In this example category 2 2910 is deactivated, as is indicated by the cross hatching. In such an instance, the questions within category 1 2908 are asked, category 2 is skipped because it is deactivated, and the execution flow proceeds to category 3 2912 and category 4 2914. As is discussed later, it is possible for any number of categories to be activated or deactivated and it is also possible to activate or deactivate categories based on a predetermined schedule such as activating or deactivating categories based on the day of the week. For example, category 2 2910 may be activated on Mondays, Wednesdays and Fridays and deactivated on Tuesdays, Thursdays, Saturdays and Sundays. Similarly, example category 4 2914 may be activated on Mondays, Tuesdays and Wednesdays, but deactivated on Wednesdays, Thursdays, Fridays, Saturdays, and Sundays. Categories may be activated and deactivated based on date ranges, as well.

Figure 30:
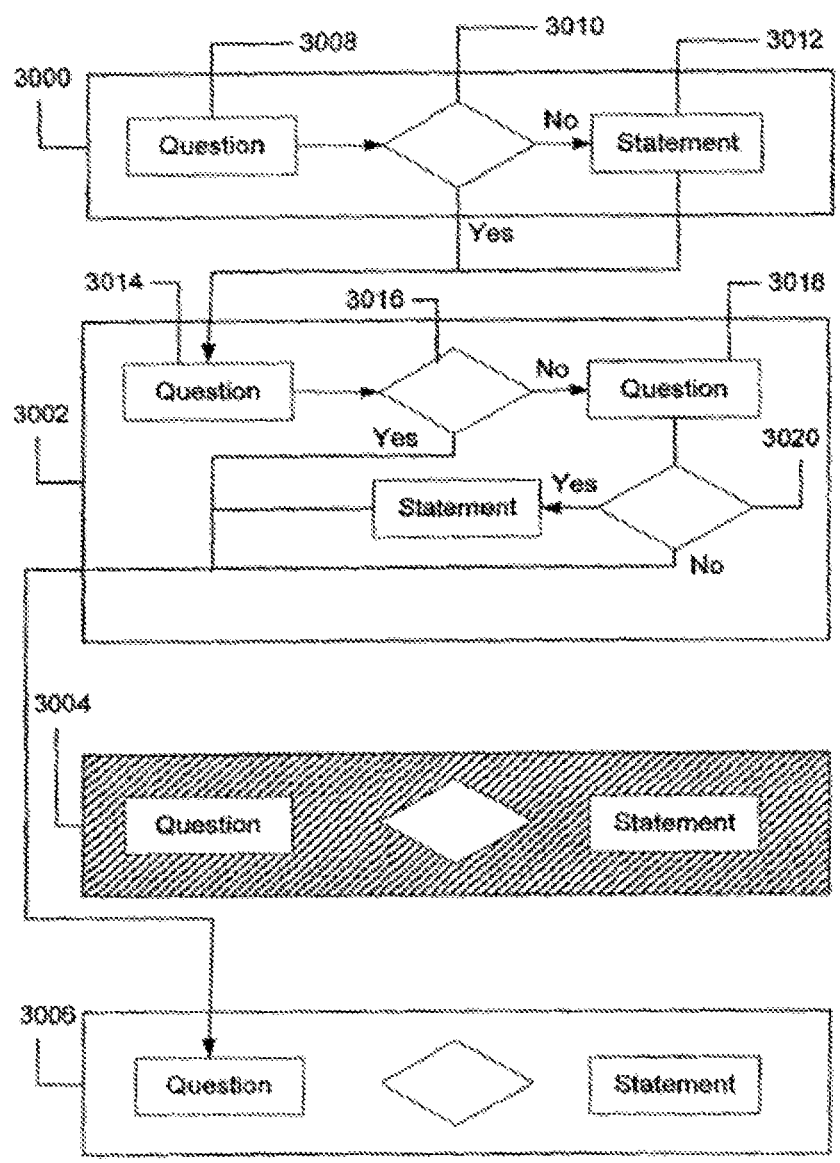
FIG. 30 depicts an exemplary question sequence composed of four categories, according to one embodiment.

FIG. 30 depicts a question sequence composed of four categories 3000, 3002, 3004, and 3006. As was the case in FIG. 29, the flow from category to category is largely sequential, in that the flow moves from category 3000 to category 3002, skips over category 3004 because it is cross hatched and depicted as deactivated for the sake of example, and proceeding on to category 3006.

Intra-category execution flow is shown for the sake of example. Turning to question category 3000, it can be seen that therein is included a question 3008 followed by a branch instruction 3010. If, for example, category 3000 were related to the topic of overeating, question 3008 may read "did you eat more than three meals today?" At branch instruction 3010 the answer of the person using the monitoring unit is evaluated, and the flow of execution is directed based on the person's answer. For example if the person answered "no," i.e., he did not eat more than three meals that day, the flow may go on to statement instruction 3012, which may be a praise statement. For example praise statement 3012 may read "good job." Execution flow would then move on to category 3002. On the other hand, if the person answered that he had eaten more than three meals, execution flow would have moved from branch instruction 3010 directly to category 3002.

Category 3002 shows an intra-category execution flow that is a little more complicated than the one shown with reference to category 3000. Assuming for the sake of example that question category 3002 was directed toward the topic of emotional eating, then question 3014 may read "were you happy today?" The flow then moves on to branch instruction 3016. If the person had answers "yes," flow proceeds on to the next active question category, question category 3006 (because question category 3004 is depicted as being deactivated). On the other hand, if the person answers "no" to the question "where you happy today," then flow proceeds from branch instruction 3016 to follow-up question 3018, which may read "did you eat to feel better?" The person's answer is evaluated at branch instruction 3020. Assuming the person answered that he did not eat to feel better, once again flow would move on to question category 3006. On the other hand, if the person answered that he had eaten to feel better, then execution flow moves on to reminder statement 3022 which may read "Remember to stick to your meal plan." Thereafter execution flow would move on to category 3006.

Thus, as can be seen from the preceding example, question categories 3000, 3002, 3004, and 3006 may include: (1) questions related to a topic; (2) branch instructions that control the flow of execution based upon the person's answer to the questions; (3) follow-up questions; and (4) praise or reminder statements based upon the person's answers to the questions. Generally, the flow from category to category is sequential, although this is not necessary. Generally, execution flow skips over deactivated question categories and proceeds on to the next active question category.

Figure 31:
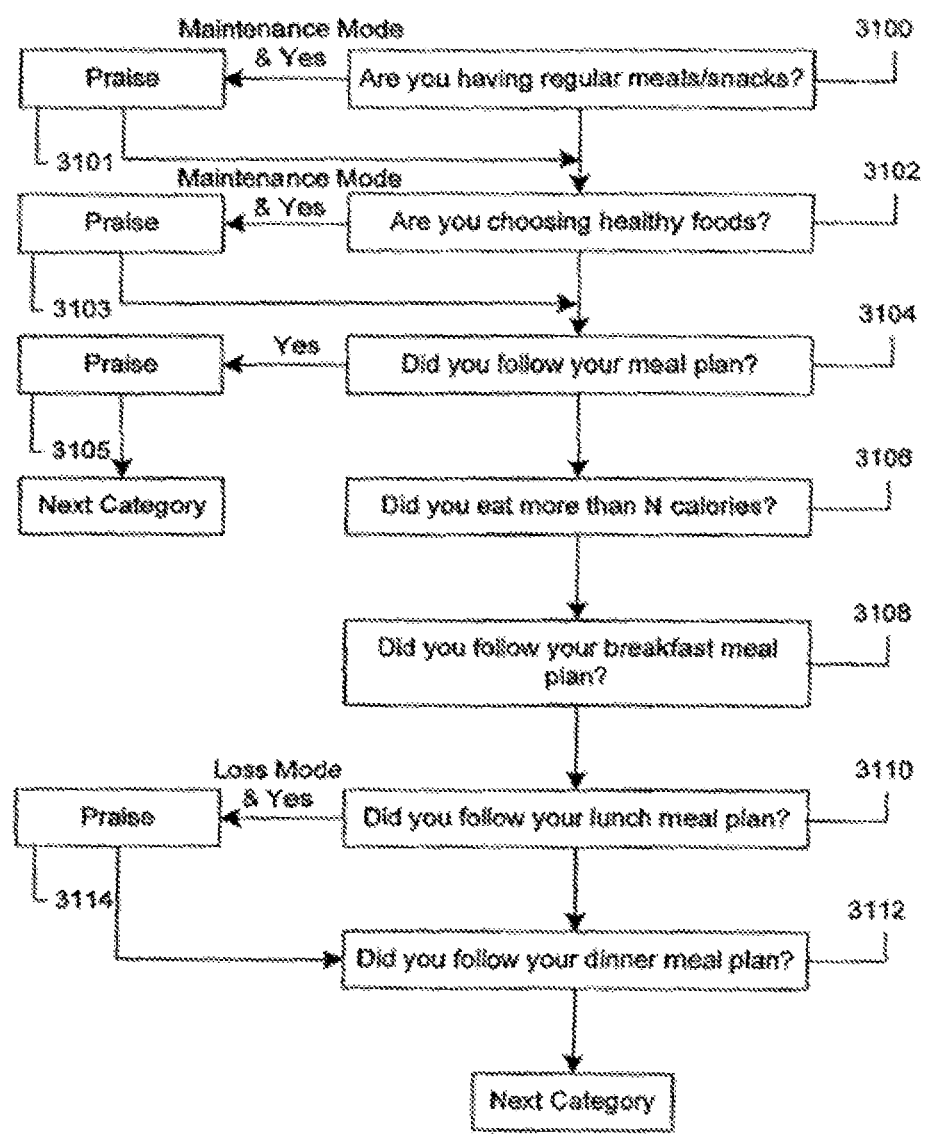
FIG. 31 depicts a questioning scheme influenced by a mode of operation, according to one embodiment.

FIG. 31 depicts a question set having questions 3100, 3102, 3104, 3106, 3108, 3110, and 3112. The question set in FIG. 31 is directed toward the topic of meal planning. Thus each question within this category relates to determining whether the person using the monitoring unit exhibited deliberate dietary habits throughout the day.

FIG. 31 also depicts the principle that the monitoring unit, such as monitoring unit 14, may be put into a mode of operation. In the case wherein monitoring unit 14 is programmed for the purpose of encouraging weight loss or weight management, the monitoring unit may be programmed in either a weight loss mode or a weight management mode. Execution flow within a question category may be altered depending upon the mode that the monitoring unit is in. This principle is illustrated in FIG. 31.

Execution flow begins with question 3100: "Are you having regular meals/snacks?" If the person answers "yes," and if the monitoring unit is in weight management mode, execution flows to praise statement 3101, which may read, "You are focused on your goals!" Thereafter, execution flow proceeds to question 3102. On the other hand, if the monitoring unit is in weight loss mode, execution flow moves on to question 3102, regardless of the person's answer. Question 3102 reads, "Are you choosing healthy foods?" Once again, if the person answers "yes," and if the monitoring unit is in weight management mode, execution flow moves on to praise statement 3103, which may read "Great job with this system! Keep it up!" As before, if the monitoring unit is in weight loss mode, execution flow moves on to question 3104, irrespective of the person's answer. Question 3104 reads "did you follow your meal plan?" If the person answers "yes," execution flow moves on to praise statement 3105. Praise statement 3105 may be different based upon whether the monitoring unit is in weight loss mode or weight management mode. For example, if the monitoring unit is in weight loss mode, praise statement 3105 may read, "You're on your way to success." If on the other hand the monitoring unit is in weight management mode, praise statement 3105 may read, "Good job!" Thereafter as can be seen from FIG. 31 the remaining questions in this question category are skipped and the next activated category is executed. On the other hand if the person were to answer "no" to question 3104, execution flow moves on to question 3106, which reads "Did you eat more than N calories". "N" is a variable which may be set by the remote computer, such as the remote computer 32 depicted in FIG. 4, and may be individualized for a particular user. Thereafter, execution flow moves on to question 3108, which reads "Did you follow your breakfast meal plan?" Irrespective of the person's answer, execution flow moves on to question 3110, which reads "Did you follow your lunch meal plan". If the person answers "yes," and the monitoring unit is in weight loss mode, execution flow moves on to praise statement 3114, which may read "Great job with this system! Keep it up!" Thereafter, execution flow moves on to question 3112. On the other hand, if the monitoring unit is in weight management mode execution flow moves from question 3110 to question 3112 irrespective of the person's answer. The final question in the exemplary question category reads "did you follow your meal plan?" Upon answering this question execution flow moves on to the next active category.

Although FIG. 31 shows specific questions that may be included within a question category directed to meal planning, other question categories may exist in a system for weight loss or weight management. Those categories may include categories directed toward dietary recording, overeating, skipping of meals, eating at home, portion size, eating out, grocery shopping behavior, label reading, water consumption, happiness, stress, depression, support, body image, fit of clothing, body measurements, program satisfaction, exercise and lesson plans.

In sum, FIG. 31 depicts the following general principles. The monitoring unit may be programmed to be in one of a plurality of modes of operation. Based on the mode of operation, the monitoring unit may alter intra-category and/or inter-category execution flow. For example, the monitoring unit may ask a different follow-up question, may give a different praise or reminder statement, may execute a different category, may omit a follow-up question, and/or may omit a praise or reminder statement, based upon the selected mode of operation. Although not depicted by FIG. 31, each of the questions (such as 3100-3112) within a category are individually activatable and deactivatable. Individual questions may be activated or deactivated according to a schedule, or may be activated or deactivated indefinitely. For example, any question within a group may be deactivated for a given use, although the group as a whole may be active. Thus, for example, the question "Are you choosing healthy foods?"

(question 3102) may be activated on Mondays, Wednesdays and Fridays, but deactivated on Tuesdays, Thursdays, Saturdays and Sundays. Conversely, a question may be activated, although the group in which the question resides is deactivated. Such programmability permits a manageable number of questions to be presented to the person using the monitoring unit. Further, such programmability allows the person's experience to vary from day to day, so that the person maintains his or her interest in the unit.

Figure 32:
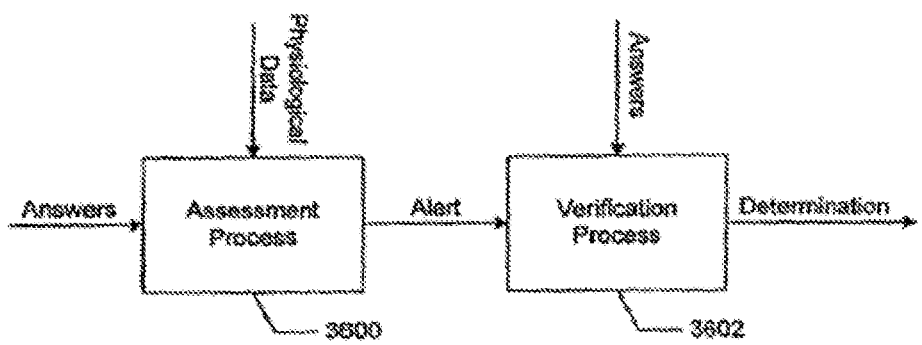
FIG. 32 depicts an interactive system of assessment and verification of an alert generated by a patient monitoring system, according to one embodiment.

FIG. 32 depicts a patient monitoring scheme wherein an alert is initially generated, and subsequently verified. As can be seen from FIG. 32, the scheme includes two processes: an assessment process 3600 and a verification process 3602. According to the scheme of FIG. 32, a patient monitoring device (such as the patient monitoring devices 1100 or 2100 depicted in FIGS. 11 and 21, respectively) may be configured to measure at least one physiological parameter exhibited by a patient, and to prompt the patient with a set of questions. As described previously herein, the physiological parameter may include the patient's weight, the patient's blood glucose level, the patient's transthoracic impedance, etc. As also described previously herein, the questions may relate to the patient's perception of his or her physical condition (example: "Do your ankles exhibit swelling?" or "Do you feel shortness of breath when you exercise?").

Upon acquisition of the physiological data and patient answers, an initial assessment process 3600 is initiated. The assessment process 3600 may be performed by the patient monitoring device (such as the base receiver 108 of FIG. 1), or may be initiated by a remote computing system (such as the remote care system 110 of FIG. 1) with which the patient monitoring device communicates. The assessment process analyzes the patient answers and physiological data, as described previously herein, in order to arrive at a preliminary conclusion regarding whether the patient may need medical attention (for example, a preliminary conclusion may be drawn that the patient is experiencing an acute episode of a chronic disease, and therefore receive further medical attention). If the assessment process 3600 determines that the patient may need medical attention and/or further clinical triage, an alert is generated. As used herein, the terms "alert" and "exception" are synonymous.

In response to the generation of an alert, a verification process 3602 is initiated. The verification process 3602 involves analysis of both the data set (answers and physiological data) operated upon by the assessment process 3600 and additional data. The additional data may come in the form of additional patient answers to additional questions. On the basis of the original data set and the additional data, a determination is made whether the patient actually needs medical assistance.

Traditionally, the verification process 3602 has been performed by trained medical personnel, such as by a nurse, case manager or disease manager. Typically, a nurse obtains the original data set that was the basis for the alert, and examines the information therein. Thereafter, the nurse places a telephone call to the patient, and questions the patient further, in order to determine if further medical intervention is required.

On any given day, a call center may expect to observe an alert generated by 10%-20% of its telemonitored patient populace. A typical nurse can perform on the order of forty to fifty calls per day, meaning that a single nurse can manage on the order of 250 patients. From these FIGUREs, it can be seen that the number of patients a particular call center can manage is directly related to the number of nurses or operators employed. Unfortunately, nurses are oftentimes in short supply and may be expensive. Therefore, employment of a multitude of nurses tends to drive health care costs up, and perhaps prevents some of the populace from obtaining the health care services they need.

Figure 33:
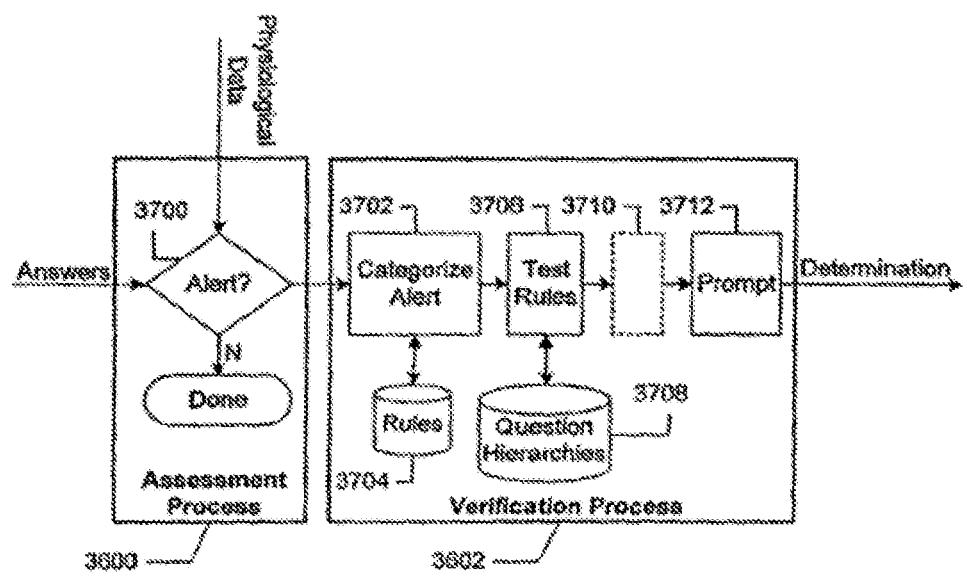
FIG. 33 depicts an embodiment of the system of FIG. 32, according to one embodiment.

To address the aforementioned challenge, the verification process 3602 may be automated, so as to reduce or eliminate the need for nurse involvement in the process 3602. FIG. 33 depicts a kernel for automation of the assessment and verification scheme presented in FIG. 32.

The kernel depicted in FIG. 32 includes modules. The modules may be embodied as software, firmware, or hardware, such as one or more application-specific integrated circuits (ASICs), as is understood by those of skill in the art. As can be seen, the kernel of FIG. 32 includes modules for implementation of the assessment and verification processes 3600 and 3602 described with reference to FIG. 31. For example, the kernel includes an alert generation module 3700. The alert generation module 3700 receives the physiological data and answers from the patient, and determines whether an alert should be generated. Examples of processes by which this initial assessment may be made are disclosed above, and are therefore not presently reiterated. If no alert is generated, no verification is needed, and the process may halt. On the other hand, if an alert is generated, then a verification process 3602 is initiated. Such process may begin immediately after a single data element is input (such as a single answer or single physiological data element). Such a single element may begin the interactive assessment and verification process. Such an interactive process may also be used to provide immediate patient self-management feedback and recommendations. In other words, reception of a single answer or physiological parameter may constitute a sufficient basis upon which an assessment process may generate an alert. Accordingly, the verification process may commence after the reception of but a single answer or physiological parameter.

To effect verification 3602, the original data set, which was the basis of the alert, may be received by a categorization module 3702. The categorization module 3702 assesses the original data, in order to classify the alert in one or more categories. A category is a broad articulation of why the alert was generated. For example, an alert may be classified as a "high weight" alert, meaning that the alert was generated because the patient's weight exceeds some threshold. Thus, "high weight" is an example of a category. Additionally, an alert may be classified "symptom score" alert, meaning that the patient's answers corresponded to a score exceeding a threshold. Examples of schemes for scoring of a patient's answers and for comparison of the score to a threshold are described previously herein, and are therefore not presently discussed further. Other examples of assessments, categories and alerts are known, and other examples may readily present themselves to those of skill in the art. Furthermore, other examples may be derived and presented in many forms, which may include but are not limited to statistically validated surveys such as the Kansas City Quality of Life, SF-12, SF-36, and others. Such assessments, categories, and alerts are within the scope of the present invention.

In the wake of having classified the alert as falling into one or more categories, recognizing that a single alert may comprise its own category, a data store 3704 of rules is accessed. The data store 3704 contains a set of rules corresponding to each category. A rule or rule set is retrieved for each category in which the alert was classified. For example, if the alert was categorized as falling within two categories (e.g., "high weight" and "symptom score"), then two rule sets are retrieved (e.g., one rule set corresponding to "high weight" and another rule set corresponding to "symptom score").

However, according to some embodiments, one or more rules or rules sets may be retrieved in the absence of having categorized the alert. In any event, thereafter, the rule set(s) are passed to a testing module 3706. The testing module 3706 tests the original data set against each rule within each retrieved rule set, and identifies which rules are "triggered." A rule is said to be "triggered" if its assessment results in an affirmative result or a Boolean "1".

A rule set is composed of various rules that the original data set, and/or historical recordings of past original data sets, and/or other data collected by the central computing system may be tested against to better understand the nature and/or cause of the alert. Therefore, each triggered rule may correspond to a hypothesized nature or cause of the alert, which may, in turn, correspond to a line of questioning helpful in exploring the hypothesized nature or cause. For example, Table 6 (below) presents a rule set corresponding to a "high weight" alert.

TABLE 6

Rule Set: High Weight

| | |
|---|---|
| Rule #1 | Minimal Weight Gain & No Alert Over Past 20 Days |
| Rule #2 | Minimal Weight Gain & Alert For Two Or More Days |
| Rule #3 | Minimal Weight Gain & Positive Weight Trend |
| Rule #4 | Minimal Weight Gain & Report Of Missed Medication |
| Rule #5 | Minimal Weight Gain & Medication Side Effect |
| Rule #6 | Minimal Weight Gain & Hospitalized in Past 14 Days |
| Rule #7 | Moderate Weight Gain & No Alert Over Past 20 Days |
| Rule #8 | Moderate Weight Gain & Alert For Two Or More Days |
| Rule #9 | Moderate Weight Gain & Positive Weight Trend |
| Rule #10 | Moderate Weight Gain & Report Of Salty Meal |
| Rule #11 | Moderate Weight Gain & Report Of Missed Medication |
| Rule #12 | Moderate Weight Gain & Medication Side Effect |
| Rule #13 | Moderate Weight Gain & Hospitalized in Past 14 Days |
| Rule #14 | Moderate Weight Gain & No Alert In Past 7 Days |
| Rule #15 | Significant Weight Gain |
| Rule #16 | Weight Gain For Two Or More Days |
| Rule #17 | Minimal Weight Gain & Report Of New Or Increased Symptoms |
| Rule #18 | Moderate Weight Gain & Report Of New Or Increased Symptoms |
| Rule #19 | Moderate Weight Gain Exhibited Over A Single Day |
| Rule #20 | Minimal Weight Gain Exhibited Over Past Two Days |
| Rule #21 | Moderate Weight Gain Exhibited Over Past Two Or More Days |
| Rule #22 | Minimal Weight Gain For One Day & No Symptoms |
| Rule #23 | Minimal Weight Gain For One Day & Usual Symptoms Reported |
| Rule #24 | High Trigger Weight Change Within Minimal Weight Range & Current Weight Is Less Than Last Reported Weight |
| Rule #25 | Moderate Weight Gain Over High Weight Trigger & Weight Decreased From Previous Day & Usual Symptoms |
| Rule #26 | High Trigger Weight Change Within Minimal Weight Range & Current Weight Is Less Than Last Reported Weight & Hospitalized For CHF Within Past 14 Days |
| Rule #27 | Moderate Weight Gain Exhibited Over A Single Day & No Symptoms |

As mentioned previously, the testing module 3706 tests the original data set against each rule within each retrieved rule set, and identifies which rules are triggered. For each rule that is triggered, a question hierarchy is retrieved from a data store 3708. Of course, although FIG. 37 depicts data stores 3704 and 3708 as being distinct from one another, the data stores 3704 and 3708 may be embodied as a single data store. A question hierarchy includes a set of questions. Each question has an answer that may be selected from a set of discrete answers (e.g., "true-or-false," or "a, b, c, or d"). The question may be posed to the patient, who selects an answer from amongst the set of discrete answers. On the basis of the patient's answer, a subsequent question is posed, and/or an instruction is given, and/or a conclusion is reached, and/or an action is carried out. The answer to the subsequent question, and/or the outcome of the action undertaken determines the next question to be posed, and/or instruction to give, and/or conclusion to reach, and/or action to undertake, and so on. Each question hierarchy is configured to explore the hypothesized nature or cause deduced from a given triggered rule. Examples of question hierarchies are presented with reference to FIGS. 20-28 herein, and are therefore not presently discussed further. Of course, one skilled in the art of medical diagnosis may readily create question hierarchies directed to exploration of triggered rules, and such question hierarchies are within the scope of the present invention. After retrieval of the question hierarchies from the data store 3708, some optional operations may be performed upon the hierarchies by an optional preparation module 3710. For example, the preparation module 3710 may inspect the retrieved question hierarchies for questions included in more than one such hierarchy. The preparation module may remove redundant questions, so that a given question is posed but a single time to the patient. Further, the preparation module 3710 may examine the question hierarchy to determine if any of the questions therein have already been posed to the patient prior to the initial assessment process 3600. If so, the answers thereto may be extracted from the original data set and inserted into an appropriate data space in the question hierarchy, so that the patient is not re-asked a question that he or she was asked by the monitoring device. Further, the preparation module 3710 may determine that the question hierarchy requires modification based on the patients co-morbidities. Further, the preparation module 3710 may examine prior questions posed to the patient and determine such new questions are inappropriate.

In the wake of operation of the optional preparation module 3710, the question hierarchies are presented to the patient via a prompting module 3712. According to one embodiment, the prompting module 3712 may guide an operator through a series of questions, which the operator poses to the patient via the telephone. For example, a first question may be presented to the operator via an output device. The operator may pose the question to the patient, obtain the patient's answer, and enter the answer via an input device, thereby obtaining a second question (or instruction, etc).

Alternatively, all of the modules 3700, 3702, 3706, 3710, and 3712 and data stores 3704 and 3708 may be programmed into a memory device in the patient monitoring apparatus. Alternatively, all of the modules 3700, 3702, 3706, 3710, and 3712 and data stores 3704 and 3708 maybe programmed into an interactive television module or web interface. For example, the base receiver 108 of FIG. 1 may include memory devices storing the aforementioned modules, so that both the assessment process 3600 and the verification process 3602 are performed by the patient monitoring device.

Whether the modules are embodied in software/firmware stored in the patient monitoring device, or whether they are stored in the remote computing system, the outcome of presentation of the question hierarchies to the patient may include a determination of whether or not the patient needs to consult with a health care professional or otherwise see or speak with a physician or nurse. Other outcomes are possible. For example, the verification process 3602 may interact with software executed by the remote computing system. Such software is described in U.S. patent application Ser. No. 10/788,900, filed on Feb. 27, 2004 by Cosentino, and entitled "SYSTEM FOR COLLECTION, MANIPULATION, AND ANALYSIS OF DATA FROM REMOTE HEALTH CARE DEVICES," which is hereby incorporated by reference. According to one embodiment, the software is configured to interact with the verification process 3602, so as to automatically create a follow-up entry or an intervention entry, when appropriate. For example, if the question hierarchy arrives at a point whereby an instruction is given to the patient to increase his medication dosage, an intervention entry is automatically created reflecting this action. Similarly, if the question hierarchy arrives at a conclusion that a follow-up action must be taken in the future, a follow-up entry reflecting this conclusion may be automatically created.

Figure 34:
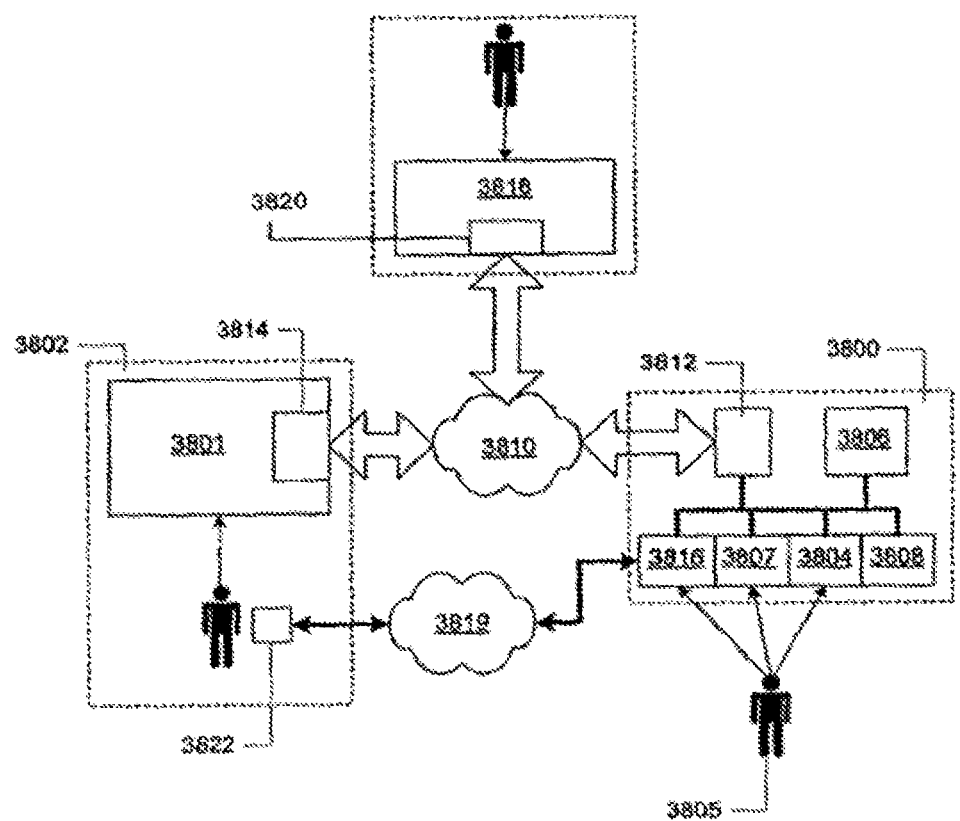
FIG. 34 depicts an embodiment of a patient monitoring system, according to one embodiment.

According to one embodiment, the outcome of the verification process 3602 or assessment process 3600 may initiate a data communication (e.g., telephone call, page, short message service exchange, etc.) to medical office or call center. For example, traversal of a question hierarchy may lead to a conclusion that a nurse or other professional needs to be contacted, to schedule a medical appointment, for example, or for further assessment of the patient, or for other medical care plan management. At such a juncture, the patient monitoring apparatus automatically initiates a data transmission, telephone call, or other communication session to the appropriate network address, telephone number, or receiving location. For example, the data transmission may be carried out by a modem, telephone, cellular telephone, television, pager, hand-held wireless device, or other apparatus, that is integrated with, or otherwise in communication with, the patient monitoring device. An example of such a system is depicted in FIG. 34. FIG. 34 is a high-level depiction of a monitoring system employing the aforementioned embodiment. As can be seen from FIG. 34, the system comprises a patient monitoring apparatus 3800, a central computer 3801, and a computer system 3818 located at an oversight association, such as an HMO. The central computer 3801 is housed within a facility 3802 that is located remote from the patient monitoring apparatus 3800. For example, the patient monitoring apparatus 3800 may be located in the home of an ambulatory patient 3805, while the central computer 3801 is located in a call center, disease management company or health care facility 3802. The central computer may be coupled to a communication network 3810 or 3819, such as to the Internet, public switched telephone network, or other network.

As described previously, the patient monitoring apparatus 3800 is composed of a central processor unit 3806, which is in communication with an input device 3807, an output device 3804, and a memory device 3808. The memory device 3808 may have each of the modules and data stores described with reference to FIG. 33 stored therein. Additionally, the memory device 3808 may have a telephone number or network address, etc. to contact in the event that a nurse follow-up telephone call or communication session is necessitated stored therein.

As discussed previously, the output device 3804 may be used to prompt the patient 3805 with questions regarding the patient's wellness and may also provide immediate feedback to the patient based on such answers. The output device 3804 may consist of a visual display unit such as LCD, touchscreen or television that displays the questions in a language of the patient's 3805 choosing. Alternatively, the output device 3804 may consist of an audio output unit that vocalizes the questions and combined with an input device such as an interactive voice response system records such answers. In one embodiment, the audio output unit 3804 may vocalize the questions in a language of the patient's 3805 choosing. As yet another alternative, the input device 3807 and output device 3804 may be embodied jointly as an interactive voice response system. The patient monitoring apparatus 3800 communicates with the central computer 3801 via a network 3810; the patient monitoring apparatus 3800 uses a communication device 3812 to modulate/demodulate a carrier signal for transmission via the network 3810, while the central computer 3801 uses a communication device 3814 for the same purpose. Examples of suitable communication devices 3812 and 3814 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network. Of course, the oversight association's computer 3818 may use a similar communication device 3820 for the same purpose, as well. The patient monitoring device 3800 may include a physiological parameter transducer (not depicted) in data communication with the processor 3806. Alternatively, the patient monitoring device 3800 may couple to an external physiological parameter transducer through an input/output port, for example. Alternatively, the patient monitoring device may communicate via telemetry, RF transmission, or other wireless means with an implanted device such as a pacemaker, defibrillator or synchronization device as described above in the present document. For example, a portion or all of the physiological parameter data may be communicated to the patient monitoring device from an implantable medical device, such as a pacemaker, defibrillator, cardiac ˆsynchronization therapy (CRT) device, stimulator, etc. Additionally, the patient monitoring device 3800 may exclude a physiological transducing unit altogether. If during traversal of the question hierarchies, it is determined that a data transmission should be initiated with a medical attendant (e.g., a nurse, physician, health care attendant, etc.), then the patient monitoring device 3800 may initially transmit the data set operated upon by the verification process (or some subset thereof) to the central computer system 3801 (this is an optional step).

Next, the patient monitoring device 3800 may attempt to establish a two-way communication session with a nurse or other professional at the call center, clinic, etc. 3802. The two-way communication session may occur as a computer-to-patient monitoring device session transacted through the network 3810. Per such a scenario, the nurse or other professional could observe the data set initially transmitted to the central computer 3801, and could then join the electronic two-way communication session to make further inquiry of the patient 3805.

Alternatively, the patient monitoring apparatus may make use of another communication device 3816, by which a communication session is initiated with another communication device 3822 accessed by the professional at the call center 3802. For example, the communication device 3822 may be a telephone, a cellular telephone, a pager, a Blackberry® device, or other wireless communication device. The communication device 3816 utilized by the patient monitoring device 3800 may initiate a communication session with the professional's device 3822, so that two-way communication may be established. Per this scenario, the data set operated upon by the verification process (or some subset thereof) may be transmitted from the patient monitoring device 3800 to the professional's communication device 3822. As an alternative, the central computing system 3801 may communicate the information to the professional's communication device 3822. In either event, at the time that the two-way communication session is initiated, the professional has access to the information, so that the professional has data that serves as the basis for further inquiry of the patient 3805.

In the event that the communication device 3816 is embodied as a telephony device, then the processor 3806 may initiate a telephone call via a telephone unit 3816 under the control of the processor 3806. The telephone unit 3816 may be instructed of the appropriate number to call by the processor 3806, or may be preprogrammed to call a specific telephone number. Thus, immediately at the time the question hierarchy is interacting with the patient, a nurse may be called, thereby saving the nurse time and effort of having to initiate the telephone call. In the event that the communication device 3812 is a telephone modem, the telephone unit 3816 may be integrated as a part of the modem 3812, with an external speaker and microphone coupled thereto for facilitation of conversation between the nurse and the patient. Alternatively, if embodied as a distinct device, the unit 3816 may include a speaker and microphone suitable for enablement of "speaker phone" communication. It is possible that, for one reason or another, the two-way communication session cannot be established (example: communication devices 3816 and 3822 are telephonic devices, and the call center's 3802 telephone lines are busy). In such an instance, subsequent re-attempts to establish the communication session may be initiated by the patient monitoring apparatus 3800. If, however, a threshold number of re-attempts (e.g., twelve re-attempts) prove fruitless, then a data transmission may be made to the computer system 3818 at the oversight association. According to one embodiment, the patient monitoring device initiates the data transmission to the computer system 3818, and transmits a data packet containing content sufficient to inform that oversight association's computer 3818 that the patient 3805 has not yet been contacted. According to one embodiment, the aforementioned data packet may have a unique code associated therewith. Thus, when a two-way communication session is finally established between the patient and the professional, a corresponding code may be transmitted from the professional's communication device 3822 or computer system 3801 to the oversight association's computer 3818 to confirm that the patient 3805 has been contacted.

Figure 35A:
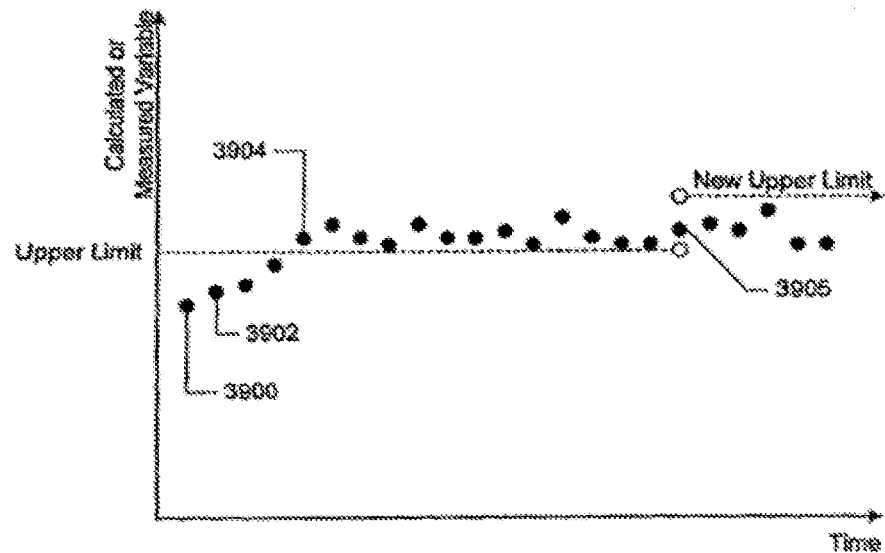
FIG. 35A depicts a Cartesian plane presenting a measured or calculated parameter that is compared with a threshold.

When managing large patient populations, constant parameter adjustment is required. Such parameter adjustment for biometric measurements, symptom thresholds and other parameters requires a skilled resource and can be time intensive. The central computing system (such as computing system 3801) may be programmed to automatically readjust certain parameters from time to time. The graph depicted in FIG. 35A presents a background for understanding this feature. A Cartesian plane is depicted in FIG. 35 A, with a measured or calculated variable presented along the y-axis, and successive measurements presented along the x-axis. The measured variable describes a quantifiable condition or state of the patient's body. For example, the measured variable may be weight, blood glucose, blood oxygen level, blood pressure, transthoracic impedance (examples of measured variables), or may be a score describing a patient's self-reported symptoms (an example of a calculated variable). Oftentimes, such scores are monitored as a part of the assessment process 3600 (FIG. 32), as has been described above. An alert may be generated when the score exceeds a threshold (or falls beneath a threshold), when a score exhibits a sustained trend (e.g., weight increase exhibited over the span of at least N days), or when a score as measured or calculated on a given day differs from a score as measured or calculated on a previous day by more than a prescribed quantity, etc.

Notably, each of the aforementioned sorts of variable monitoring schemes shares a common premise, namely, that a change in the monitored variable's value corresponds to a change in the chronic condition being monitored. Sometimes, however, this premise is incorrect. For example, a patient's weight may vary because the patient is experiencing an acute episode of pulmonary edema, in which case the premise is correct—the change in the patient's weight over time reveals a change in the state of the chronic condition. On the other hand, a patient's weight may vary over time because the patient has gained or lost fatty or muscular tissue. Per such a scenario, the change in the patient's weight is unrelated to the chronic condition being monitored.

As mentioned above, in some instances an alert may be generated in the event that the measured variable exceeds or falls short of a threshold. Such a strategy may prove unreliable in the situation where the monitored variable has exhibited change for reasons unrelated to the chronic condition being monitored. With respect to FIG. 35A, one may assume, for the sake of illustration, that the measured variable is a patient's weight, and that each darkened dot on the Cartesian plane represents a given daily weight measurement for a particular patient. Thus, point 3900 represents a particular patient's weight on a given day, and point 3902 represents the patient's weight as measured on a successive day, and so on.

Examination of the graph of FIG. 35A reveals that on the day that the point 3904 was measured, the patient's weight exceeded an upper limit threshold, meaning that the initial assessment process 3600 (FIG. 32) would have generated an alert or exception that day. In response thereto, a verification process 3602 (FIG. 32) would have been initiated, and for the sake of illustrating the foregoing concepts, one may assume that the verification would have turned out to be negative (i.e., an interview of the patient would reveal that the patient did not need medical attention). As shown in FIG. 35A, a similar result would have occurred for fourteen consecutive days.

After two weeks of generating an alert, and thereby initiating a verification process, the software on the central computing system (or patient monitoring device, if implemented thereupon) may be programmed to re-establish a new threshold, as shown in FIG. 35A. The premise for the re-establishment is that the patient has simply gained weight, and is not experiencing edema, so the upper limit should be modified.

Figure 35B:
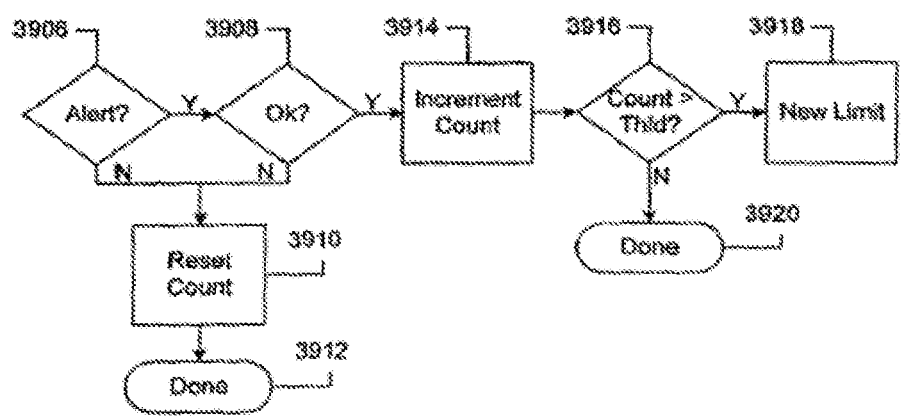
FIG. 35B depicts a scheme for altering the threshold depicted in FIG. 35A, according to one embodiment.

FIG. 35B depicts one method for altering a threshold. As shown therein, the process begins by determining whether, for a given monitored parameter, that parameter has caused an alert during the assessment process 3600 (FIG. 32), as shown in operation 3906. If so, control is passed to operation 3908, whereupon it is determined whether the subsequent verification process 3602 (FIG. 32) has shown the patient to not be in need of medical assistance. If the answer to either of these inquiries 390S is in the negative, then control is passed to operation 3910, whereupon a count variable is reset to zero, and the process is halted (operation 3912). On the other hand, if the answer to both of the inquiries of operations 3906 and 3908 is in the affirmative, the count variable is incremented (operation 3914), indicating that another day has transpired whereby a particular variable generated an alarm, but the patient has proven to be in satisfactory condition. In operation 3916, the count variable is compared against a threshold, which may be selectable. For example, the threshold may be equal to fourteen days, as shown in the example of FIG. 35A. If the count variable exceeds the threshold, the threshold(s) against which the variable is tested for generation of an alert may be adjusted (operation 3918). Otherwise, the process is halted (operation 3920). There exist many possibilities for adjusting such a threshold. For example, the software may be programmed to find a measure of central tendency over a span of the preceding N days. Then, an offset variable may be added (and/or subtracted) to the central tendency, to generate a new upper threshold and/or lower threshold. For example, in the context of the graph of FIG. 35A, execution of operation

3918 may include finding the average patient weight over the fourteen-day period preceding the measurement of point 3905. Then, an offset variable may be added to the average value, creating an upper threshold limit, and an offset value may be subtracted therefrom, yielding a lower threshold limit. Of course, other measures of central tendency may be used, such as arithmetic mean, geometric mean, median, etc. Also, other schemes for adjusting a threshold on the basis of observed historical data may readily present themselves to ones of ordinary skill in the art, and are within the scope of the present invention.

Additional details regarding the patient monitoring apparatus are disclosed in U.S. patent application Ser. No. 11/345,956 entitled "Multiuser wellness parameter monitoring system," which is hereby incorporated by reference.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method, comprising:
   receiving an emergency signal from a personal emergency device;
   contacting an emergency system after receiving the emergency signal;
   transmitting medical information and personal information about a user associated with the personal emergency device to the emergency system, wherein the medical information was collected and stored during remote monitoring of the user; and
   activating a speaker phone to automatically answer a next phone call upon contacting the emergency system such that the emergency system can attempt to communicate directly with the user.

2. The method of claim 1, in which contacting the emergency system comprises contacting a remote care system.

3. The method of claim 1, in which transmitting medical information further comprises transmitting current medical information.

4. The method of claim 1, in which contacting the emergency system comprises contacting an emergency call center.

5. The method of claim 4, in which receiving a notification at the emergency system comprises receiving a wireless signal.

6. The method of claim 5, in which receiving the wireless signal comprises receiving a Bluetooth signal.

7. The method of claim 1, in which transmitting medical information further comprises transmitting trended medical information.

8. The method of claim 1, in which transmitting medical information further comprises transmitting an exception report.

9. The method of claim 1, wherein contacting the emergency system comprises contacting a remote care system.

10. The method of claim 1, wherein contacting the emergency system comprises contacting an emergency services system.

* * * * *